US009718880B2

(12) United States Patent
Bell et al.

(10) Patent No.: US 9,718,880 B2
(45) Date of Patent: *Aug. 1, 2017

(54) TREATMENT OF PAROXYSMAL NOCTURNAL HEMOGLOBINURIA PATIENTS BY AN INHIBITOR OF COMPLEMENT

(71) Applicant: Alexion Pharmaceuticals, Inc., New Haven, CT (US)

(72) Inventors: Leonard Bell, Woodbridge, CT (US); Russell P. Rother, Oklahoma City, OK (US); Mark J. Evans, Radnor, PA (US)

(73) Assignee: Alexion Pharmaceuticals, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/148,839

(22) Filed: May 6, 2016

(65) Prior Publication Data

US 2016/0244516 A1  Aug. 25, 2016

Related U.S. Application Data

(63) Continuation of application No. 13/426,973, filed on Mar. 22, 2012, now abandoned, which is a continuation of application No. 12/225,040, filed as application No. PCT/US2007/006606 on Mar. 15, 2007, now abandoned.

(51) Int. Cl.
| *A61K 39/00* | (2006.01) |
| *A61K 9/00* | (2006.01) |
| *C07K 16/18* | (2006.01) |
| *C07K 19/00* | (2006.01) |
| *A61K 31/7105* | (2006.01) |
| *A61K 38/00* | (2006.01) |

(52) U.S. Cl.
CPC ............ *C07K 16/18* (2013.01); *A61K 9/0019* (2013.01); *A61K 31/7105* (2013.01); *A61K 38/00* (2013.01); *A61K 2039/505* (2013.01); *C07K 2317/24* (2013.01); *C07K 2317/51* (2013.01); *C07K 2317/515* (2013.01); *C07K 2317/565* (2013.01)

(58) Field of Classification Search
None
See application file for complete search history.

(56) References Cited

U.S. PATENT DOCUMENTS

| 4,686,100 | A | 8/1987 | Raffin et al. |
| 5,135,916 | A | 8/1992 | Sims et al. |
| 5,660,825 | A | 8/1997 | Sims et al. |
| 6,355,245 | B1 * | 3/2002 | Evans ................. C07K 14/472 424/130.1 |
| 7,361,339 | B2 | 4/2008 | Bell |
| 7,482,435 | B2 | 1/2009 | Bowdish et al. |
| 2003/0049260 | A1 | 3/2003 | Bell |
| 2003/0049683 | A1 | 3/2003 | Bowdish et al. |
| 2004/0038308 | A1 | 2/2004 | Rother et al. |
| 2004/0219147 | A1 | 11/2004 | Bell |
| 2004/0253242 | A1 | 12/2004 | Bowdish et al. |
| 2005/0036991 | A1 | 2/2005 | Fodor |
| 2005/0169921 | A1 | 8/2005 | Bell et al. |
| 2005/0191298 | A1 | 9/2005 | Bell et al. |
| 2005/0221382 | A1 | 10/2005 | Rother |
| 2005/0226870 | A1 | 10/2005 | Wang et al. |
| 2005/0271660 | A1 * | 12/2005 | Wang ..................... C07K 16/18 424/144.1 |
| 2006/0057679 | A1 | 3/2006 | O'Keefe et al. |
| 2006/0263349 | A1 | 11/2006 | McCutcheon et al. |
| 2007/0116710 | A1 | 5/2007 | Bell et al. |
| 2009/0028850 | A1 * | 1/2009 | Rother ................... C07K 16/18 424/133.1 |
| 2009/0220508 | A1 | 9/2009 | Bell et al. |
| 2010/0068202 | A1 | 3/2010 | Bell et al. |
| 2011/0086040 | A1 | 4/2011 | Bell et al. |
| 2012/0237515 | A1 | 9/2012 | Bell et al. |
| 2012/0308559 | A1 | 12/2012 | Bell et al. |
| 2016/0376355 | A1 | 12/2016 | Bell et al. |
| 2017/0015741 | A1 | 1/2017 | Bell et al. |

FOREIGN PATENT DOCUMENTS

| CA | WO 2005110481 A2 * | 11/2005 | ............ C07K 16/18 |
| EP | 0411306 A1 | 2/1991 | |
| WO | 2004/029207 A2 | 4/2004 | |
| WO | 2005074607 A2 | 8/2005 | |
| WO | 2005110481 A2 | 11/2005 | |
| WO | 2007002571 A2 | 1/2007 | |
| WO | 2007005612 A2 | 1/2007 | |

OTHER PUBLICATIONS

Hillmen et al. "eFFECT of eCULIZUMAB on hEMOLYSIS and Transfusion Requirements in Patients With Paroxysmal Nocturnal Hemoglobinuria" nejm 350(6), 2004, pp. 552-559.*
Hillmen et al. "Effect of Eculizumab on Hemolysis and transfusion requirements in patients with paroxysmal nocturnal hemoglobinuria" NEJM, 350; 6, 2004, pp. 552-559.*

(Continued)

*Primary Examiner* — Daniel E Kolker
*Assistant Examiner* — James Rogers
(74) *Attorney, Agent, or Firm* — Tara Rahemba, Esq.; Jane E. Remillard, Esq.; Jill Gorny Sloper, Esq.

(57) ABSTRACT

Eculizumab, a humanized monoclonal antibody against C5 that inhibits terminal complement activation, showed activity in a preliminary 12-week open-label trial in a small cohort of patients with paroxysmal nocturnal hemoglobinuria (PNH). The present study examined whether chronic eculizumab therapy could reduce intravascular hemolysis, stabilize hemoglobin levels, reduce transfusion requirements, and improve quality of life in a double-blind, randomized, placebo-controlled, multi-center global Phase III trial. It has been found that eculizumab stabilized hemoglobin levels, decreased the need for transfusions, and improved quality of life in PNH patients via reduced intravascular hemolysis. Chronic eculizumab treatment appears to be a safe and effective therapy for PNH.

3 Claims, 4 Drawing Sheets

(56) References Cited

OTHER PUBLICATIONS

Appel et al. "New approaches to the treatment of glomerular diseases" Kidney International (2006) 70, S45-S50.*
69 Studies for eculizumab for clinical trials.gov, printed Feb. 28, 2017, pp. 1-3.*
Clinical Trials Identifier: NCT0098280, "Eculizumab to Treat Paroxysmal Nocturanl Hemoglobinuria" Jun. 23, 2005, pp. 1-4.*
Safety and Effectiveness of h5G1.1-mAb for dermatomyositis clinicaltrials.gov identifer NCT00005571, Apr. 25, 2000, pp. 1-4.*
Alexion Mariana Kaplan "Eculizumab" Current Opinion in Investigational Drugs 2002, 3(7): 10107-1023.*
Adis International Limited, "Eculizumab: 5G1.1, h5G1.1, Long-Acting Anti-C5 Monoclonal Antibody 5G1-1, Long-Acting Anti-C5 Monoclonal Antibody 5G1.1," Drugs in Research and Development, vol. 8 (1 ); 61-68 (2007).
Rather et al., "Discovery and development of the complement inhibitor eculizumab for the treatment of paroxysmal nocturnal hemoglobinuria," Nature Biotechnology, 25 (11) 1256-1264 (2007).
Alexion Pharma K.K. "Report on the Deliberation Results" for "Solids for intravenous infusion 300 mg", Mar. 5, 2010, pp. 1-105.
Alexion Pharmaceuticals Inc., "Alexion completes enrollment in Ph II kidney disease trial," Market letter (Feb. 25, 2002), 2 pages.
Alexion Pharmaceuticals Inc., "Alexion Completes Enrollment in Phase II Membranous Nephritis Clinical Trial with 5G1.1; 5G1.1 Receives Orphan Drug Designation in Membranous Nephritis," PR Newswire, Feb. 20, 2012, 3 pages.
Alexion Pharmaceuticals Inc., "Alexion issued C5 complement inhibitor patent for inflammatory diseases," ESPICOM Pharmaceutical and Medical Device News (Mar. 19, 2002), 1 page.
Alexion Pharmaceuticals Inc., "Alexion Issued Key C5 Complement Inhibitor Patent for Inflammatory Diseases," PR Newswire(Mar. 15, 2002) 3 pages.
Alexion Pharmaceuticals Inc., "Alexion Pharmaceuticals Reports Second Quarter and First Half Results," PR Newswire [New York] (Mar. 8, 2001) 8 pages.
Alexion Pharmaceuticals Inc., "Alexion Pharmaceuticals Reports Second Quarter and First Half Results;—Quarter Highlighted by Successful Revision of Pexelizumab Collaboration With Procter &Gamble Pharmaceuticals and Commencement of Phase III Pivotal PRIMO-CABG Trial," PR Newswire, Mar. 8, 2002, 6 pages.
Alexion Pharmaceuticals Inc., "Company reports second quarter, first-half results," Biotech Week (Apr. 10, 2002), 2 pages.
Alexion Pharmaceuticals Inc., "Eculizumab Alexion clinical data (phase III) (PNH)," R & D Focus Drug News (Feb. 6, 2006), 2 pages.
Alexion Pharmaceuticals Inc., "Eculizumab Alexion clinical data (PNH)," R & D Focus Drug News (Jan. 30, 2006), 2 pages.
Alexion Pharmaceuticals Inc., "Eculizumab Alexion completes enrollment for phase III PNH trial," R & D Focus Drug Mews, (Apr. 25, 2005): 2 pages.
Alexion Pharmaceuticals Inc., "Eculizumab Alexion completes enrollment," R & D Focus Drug News (Feb. 17, 2003), 2 pages.
Alexion Pharmaceuticals Inc., "Eculizumab Alexion Emea grants request for accelerated assessment procedure," R & D Focus Drug News (Aug. 28, 2006), 2 pages.
Alexion Pharmaceuticals Inc., "Eculizumab Alexion initiates second phase III study," R & D Focus Drug News, (Jan. 17, 2005), 2 pages.
Alexion Pharmaceuticals Inc., "Eculizumab Alexion plans phase III trials (paroxysmal nocturnal hemoglobinuria)," R & D Focus Drug News (Aug. 2, 2004), 2 pages.
Alexion Pharmaceuticals Inc., "Eculizumab Alexion Priority Review, USA (PNH)," R & D Focus Drug News (Nov. 20, 2006), 2 pages.
Alexion Pharmaceuticals Inc., "Kidney Disease; Enrollment complete for phase II membranous nephritis clinical trial with 5G1.1," Drug Week, p. 14 (Apr. 12, 2002).
Alexion Pharmaceuticals Inc., "Kidney Disease; Enrollment complete for phase II membranous nephritis clinical trial with 5G1.1," Immunotherapy Weekly, p. 18, (Apr. 10, 2002).
Alexion Pharmaceuticals Inc.,"Eculizumab Alexion phase change III, USA, Europe Canada, Australia (PNH)," R & D Focus Drug News (Nov. 15, 2004): 2 pages.
BC Cancer Agency Cancer Drug Manual, Drug Name Alemtuzumab, Jun. 1, 2013, pp. 11.
Brekke, O. et al., "Therapeutic Antibodies for Human Diseases at the Dawn of the Twenty-First Century," Nature Reviews, Drug Discovery, vol. 2: 52-62 (2003).
ESPICOM Pharmaceutical and Medical Device News, "Eculizumab found to be well tolerated and efficacious during 52 weeks of treatment in PNH," (Jan. 2, 2007), 2 pages.
European Decision Revoking the European Patent (Art. 101(2). (3)(b) EPC). 11 pages. dated Jul. 1, 2014.
European Medicines Agency, EMAIHMPC/16633/2009 section 2, Historical Data on Medicinal Use, 2010, pp. 1-40.
Fung, M. et al., "Inhibition of complement, neutrophil, and platelet activation by an anti-factor D monoclonal antibody in simulated cardiopulmonary bypass circuits," The Journal of Thoracic and Cardiovascular Surgery, vol. 122(1):113-121 (2001).
Grounds of Appeal filed on Nov. 11, 2014 in the related European Opposition, European Patent No. 1720571, pp. 1-15.
Hale, et al., "Blood concentrations of alemtuzumab and antiglobulin responses in patients with chronic lymphocytic leukemia following intravenous or subcutaneous routes of administration," (2004) Blood 224(4), pp. 948-955.
Martin, F. et al., "Pathogenic Roles of B Cells in Human Autoimmunity: Insights from the Clinic," Immunity, vol. 20: 517-527 (2004).
Mollnes, T. et al., "Strategies of therapeutic complement inhibition," Molecular Immunology, vol. 43: 107-121 (2006).
Mueller, J., "Humanized Porcine VCAM-Specific Monoclonal Antibodies with Chimeric IgG2/G4 Constant Regions Block Human Leukocyte Binding to Porcine Endothelial Cells," Molecular Immunology, vol. 34(6): 441-452 (1997).
Dsborne, R., "Alexion Offers Early, Mixedphase III Data for Heart Drug," Bioworld Today, vol. 14, Issue 151 (Aug. 6, 2003), 3 pages.
Dsbourn, J. et al., "Current methods for the generation of human antibodies for the treatment of autoimmune diseases," Drug Discovery Today, vol. 8 (18): 845-851 ( 2003).
Other News to Note, Bioworld Today (Aug. 9, 2002): 5 pages.
Pierangeli,S. et al., "Requirement of activation of complement C3 and C5 for antiphospholipid antibody-mediated thrombophilia," Arthritis & Rheumatology, vol. 52, Issue 7: 2120-2124(2005).
Ricklin, D. et al., "Complement-targeted therapeutics," Nature Biotechnology, vol. 25(11): 1265-1275 (2007).
U.S. Appl. No. 15/260,888, filed Sep. 9, 2016, Leonard Bell.
U.S. Appl. No. 15/284,015, filed Oct. 3, 2016, Leonard Bell.
U.S. Appl. No. 15/260,888, filed Dec. 22, 2016, J. Rogers.
U.S. Appl. No. 15/260,888, filed Oct. 27, 2016, J. Rogers.
U.S. Appl. No. 15/284,015, filed Nov. 1, 2016, J. Rogers.
U.S. Appl. No. 13/335,518, filed Aug. 22, 2016, P. Gambel.
U.S. Appl. No. 13/426,973, filed Mar. 22, 2012, Leonard Bell.
U.S. Appl. No. 12/225,040, filed May 13, 2009, Leonard Bell.
U.S. Appl. No. 12/621,792, filed Nov. 19, 2009, Leonard Bell.
U.S. Appl. No. 10/771,552, filed Feb. 3, 2004, Leonard Bell.
U.S. Appl. No. 11/050,543, filed Feb. 3, 2005, Leonard Bell.
U.S. Appl. No. 11/595,118, filed Nov. 8, 2006, Leonard Bell.
U.S. Appl. No. 12/902,617, filed Oct. 12, 2010, Leonard Bell.
U.S. Appl. No. 13/335,518, filed Dec. 22, 2011, Leonard Bell.
U.S. Appl. No. 13/426,973, filed Jan. 27, 2014, J. Rogers.
U.S. Appl. No. 13/426,973, filed May 31, 2013, J. Rogers.
U.S. Appl. No. 13/426,973, filed Aug. 20, 2012, J. Rogers.
U.S. Appl. No. 12/225,040, filed Sep. 22, 2011, J. Rogers.
U.S. Appl. No. 12/225,040, filed Jun. 1, 2011, J. Rogers.
U.S. Appl. No. 12/225,040, filed Apr. 11, 2011, J. Rogers.
U.S. Appl. No. 12/621,792, filed Sep. 30, 2010, P. Gambel.
U.S. Appl. No. 10/771,552, filed Dec. 22, 2008, F. Vandervegt.
U.S. Appl. No. 10/771,552, filed Mar. 21, 2008, F. Vandervegt.
U.S. Appl. No. 10/771,552, filed Aug. 10, 2007, F. Vandervegt.
U.S. Appl. No. 10/771,552, filed Feb. 26, 2007, F. Vandervegt.

(56) References Cited

OTHER PUBLICATIONS

U.S. Appl. No. 10/771,552, filed Sep. 26, 2007, F. Vandervegt.
U.S. Appl. No. 11/050,543, filed Jul. 9, 2010, P. Gambel.
U.S. Appl. No. 11/050,543, filed Apr. 2, 2008, F. Vandervegt.
U.S. Appl. No. 11/050,543, filed Oct. 10, 2007, F. Vandervegt.
U.S. Appl. No. 11/050,543, filed Jun. 11, 2007, F. Vandervegt.
U.S. Appl. No. 11/595,118, filed Jan. 21, 2011, P. Gambel.
U.S. Appl. No. 11/595,118, filed Oct. 5, 2010, P. Gambel.
U.S. Appl. No. 11/595,118, filed Jul. 7, 2010, P. Gambel.
U.S. Appl. No. 11/595,118, filed Apr. 3, 2009, F. Vandervegt.
U.S. Appl. No. 12/902,617, filed Jun. 23, 2011, P. Gambel.
U.S. Appl. No. 12/902,617, filed Apr. 4, 2011, P. Gambel.
U.S. Appl. No. 13/335,518, filed Sep. 12, 2014, P. Gambel.
U.S. Appl. No. 13/335,518, filed Feb. 6, 2014, P. Gambel.
U.S. Appl. No. 13/335,518, filed Nov. 7, 2013, P. Gambel.
Alexion receives FDA, European approval for orphan drug status of new treatment for paroxysmal nocturnal hemoglobinuria, Transplant News, Jan. 15, 2004, XP002497241;Retrieved from the world wide web at findarticles.com/p/articles/mi mOYUG/is 1 14/ai 17208612 [retrieved on Sep. 25, 2008].
"Alexion Reports Presentation of Membranous Nephritis Clinical Trails"; [online]; Alexion Pharmaceuticals: News; [Retrieved on Jun. 17, 2003]. Retrieved from the world wide web at alexionpharm.com/news/sub press.cfm?prid=241&selectyear=2002.
Araten, et al., "High incidence of thrombosis in African-American and Latin-American patients with paroxysmal nocturnal haemoglobinuria," Thromb Haemost, vol. 93:88-91 (2005).
Audebert et al., "Cerebral ischemic infarction in paroxysmal nocturnal hemoglobinuria," J. Neurol., vol .252:1379-2565 (2005).
Brodsky, "New Insights into paroxysmal nocturnal hemoglobinuria," Hematology 516:24-28 (2006).
Cella, D et al., "Linking Outcomes Management to Quality-of-Life Measurement, Oncology," Williston Park, vol. 11 (11A): 232-235 (1997).
Clague et al, "A low-hemolysis blood aspirator conserves blood during surgery," Biomed. Insrum. Technol. , vol. 29 (5):419-424 (1995).
Clinics, Biotechnology News, vol. 24(30):10 (2004).
Collard et al., "Endothelial nuclear factor-KB translocation and vascular cell adhesion molecule- 1 induction by complement: inhibition with anti-human C5 therapy or cGMP analogues," Art. Thromb. Vas., vol. 19:2623-2629 (1999).
Sierra G. et al., "Vaccine against group B Neisseia meningitidis: Protection trial and mass vaccination results in Cuba", NIPH Annals 1991 NO, vol. 14(2):195-210, (1991) ISSN: 0332-5652.
Corvini M. et al., "Complement C7 deficiency presenting as recurrent aseptic meningitis," Database accession No. NLM15328683, 1 page (2004) Database Medline [Online] US National Library of Medicine (NLM), Bethesda, MD, US; Oct. 1992 (Oct. 1992).
"Alexion Announces Presentation of Preliminary Results from Phase I Pilot Study of Eculizumab Treatment of Patients with Paroxysmal Nocturnal Hemoglobinuria"; [online]; Alexion Pharmaceuticals: News; [Retrieved on Jun. 18, 2003]. Retrieved from the world wide web at alexionpharmaceuticals.com/news/sub press.cfm?prid-242&selectyear=2002.
"Alexion Announces Results of Clinical Trial in Paroxysmal Nocturnal Hemoglobinuira Presented at the American Society of Hematology Annual Meeting"; [online]; Alexion Pharmaceuticals, Inc.; [Retrieved on Jun. 17, 2003]. Retrieved from the world wide web at noonanrusso.com/news/view newsitem.aspx?ItemID=382.
Alexion Phamaceuticals: Complement Inhibitors; [online]; [Retrieved on Jun. 17, 2003]; Retrieved from the world wide web at alexionpharm.com/techplat/complement.cfm.
Alexion Pharmaceuticals Signs Agreement with Lonza Biologics for Commercial Manufacturing; [online]; Alexion Pharmaceuitcals Inc.; [Retrieved on Jun. 17, 2003]: Retrieved from the world wide web at noonanrusso.com/news/viewnewsitem.aspx?ItemID=394.

Morris J T et al: "Recurrence of neisserial meningococcemia due to deficiency of terminal complement Domponent," Database accession No. NLM1411724, Database Medline [Online] US National Library of Medicine (NLM), Bethesda, MD, US; Oct. 1992 (Oct. 1992).
Figueroa and Densen, "Infectious Diseases Associated with Complement Deficiencies," Clinical Microbiology Reviews, vol. 4(3): 359-395 (1991).
Fitch et al., "Pharmacology and biological efficacy of a recombinant, humanized, single-chain antibody C5 complement inhibitor in patients undergoing coronary artery bypass graft surgery with cardiopulmonary bypass," Circulation 100 (25)2499-2506 (1999).
Garba and Ubom, "Total serum lactate dehydrogenase activity in acute Plasmodium falciparum malaria infection," Singapore Medical J. 46(11 ):632-634 (2005).
Garcia et al. "Effect of preservatives on IgG aggregation, complement-activating effect and hypotensive activity of hourse; polyvalent antivenom used in snakebite envenomation," Biologicals, vol. 30:143-151(2002).
Genes and Disease; [online]; Paroxysmal nocturnal hemoglobinuria; [Retrieved on 2003-06017]. Retrieved from the world wide web at ncbi.nlm.nih.gov/disease/PNH.html.
Hall et al., "Primary prophylaxis with warfarin prevents thrombosis in paroxysmal nocturnal hemoglobinuria (PNH)," Blood, vol. 102 3587-3591 (2003).
Harding, J. "Eculizumab," Drugs of the Future, Pro US Science, ES, vol. 29(7): 673-676, XP008113000 (2004).
Hill et al., "Improvement in the symptoms of smooth muscle dystonia during eculizumab therapy in paroxysmal nocturnal hemoglobinuria," Haematology, 90(12): Abstract #ECR40; (2005).
Hill et al., "Sustained Control of Hemolysis and Symptoms and Reduced Transfusion Requirements over a Period of 2 Years in Paroxysmal Nocturnal Hemoglobinuria (PNH) with Eculizumab Therapy," Blood, vol. 104:Abstract 2823 (2004) with ASH poster final 2004.ppt.
Hill et al., "Sustained response and long-term safety of eculizumab in paroxysmal nocturnal hemoglobinuria," Blood, vol. 106: 2559-2565 (2005).
Hill, et al., "Protection of erythrocytes from human complement-mediated lysis by membranetargeted recombinant soluble CD59: a new approach to PNH therapy," Blood 107(5)2131-2137 (2006).
Hillmen et al. "Effect of Eculizumab on hemolysis and transfusion requirements in patients with paroxysmal nocturnal Hemoglobinuria," N Engl J Med, vol. 350(6):552-559 (2004).
Hill et al. "Improvement in the symptoms of smooth muscle dystonia during eculizumab therapy in paroxysmal nocturnal; hemoglobinuria" Haematologica, vol. 90(online): 111-113 (2005).
Hill, et al., "Nitric oxide consumption and pulmonary hypertension in patients with paroxysmal nocturnal hemoglobinuria," Blood 106(11):Abstract 1046 (2005) XP002482085—47th Annual Meeting of the American Society of Hematology, Dec. 10-13, 2005.
Hill, "Eculizumab, for the treatment of paroxysmal nocturnal hemglobinuria," Clin. Adv. In Hermal. & Onc., XP0015384263 (11):849-850 (2005).
Hillman et al., "Effect of the complement inhibitor eculizumab on thromboembolism in patients with paroxysmal nocturnal hemoglobinuria," Blood 110(12):4123-4128 (2007).
Hillmen, et al., "Eculizumab, a C5 Complement-blocking Antibody, Abolishes Hemolysis and Renders Hemolytic Patients with Paroxysmal Nocturnal Hemoglobinuria (PNH) Transfusion Independent," 44th ASH Annual Meeting, Blood 100 (11) (Abstract No. 154) (2002).
Meyers, et al., "Management Issues in Paroxysmal Nocturnal Hemoglobinuria," International Journal of Hematology, 17:125-132 (2003).
Hillmen, et al., "The complement inhibitor eculizumab in paroxysmal nocturnal hemoglobinuria," N Engl J Med. ., vol. 355: 1233-1243 (2006).
Hillmen, et al., "The terminal complement inhibitor eculizumab reduces thrombosis in patients with paroxysmal iocturnal hemoglobinuria," Blood 108(11 ):Abstract 123 (2006) XP002482084. 48th Annual Meeting of the American Society of Hematology. Dec. 9-12, 2006.

(56) References Cited

OTHER PUBLICATIONS

Hillmen, et al., Eculizumab, a C5 complement blocking antibody, is the first therapy to reduce transfusion requirements in patients with paroxysmal nocturnal haemoglobinuria (PNH); British Journal of Haematology, vol. 121, No. Supplement 1, p. 87, XP009144758 (2003). 43rd Annual Scientific Meeting of the British Society for Haematology, Apr. 7-9, 2003.

Inoue et al., "Molecular genetics of paroxysmal nocturnal hemoglobinuria," Int J Hematol., Feb 77(2):107-112 (2003).

Int PNH Interest GRP: Diagnosis management of paroxysmal nocturnal hemoglobinuria, Blood, vol. 106 (12):3699-3709, (2005) XP002482081.

Jasinski, et al. "A novel mechanisms of complement-independent clearance of red cells deficient in glycosyl phosphatidylinositol-linked proteins" Blood, vol. 103(7):2827-2834 (2004).

Kaplan "Eculizumab Alexion," Current Opinion in Invest. Drugs, vol. 3(7),1017-1023 (2002).

Kato et al. "Deconstructing sickle cell disease: reappraisal of the role of hemolysis in the development of clinical subphenotypes," Blood Reviews, vol. 21: 37-47 (2007).

Kinoshita, Taroh, "Molecular pathogenesis of Paroxysmal Nocturnal Haemoglobinuria," XXVIth World Congress of the International Society of Haematology, Singapore, Aug. 25-29, 1996.

Lee et al., "Neisseria meningitidis Bacteremia in Association with Deficiency of the Sixth Component of Complement," Infection and Immunity, vol. 24(3): 656-660 (1979).

Luzzatto, et al., Recent advances in biological and clinical aspects of paroxysmal nocturnal hemoglobinuria, Intl. J. Hematol. 84:104-112 (2006).

Macneil, "Eculizumab could be paroxysmal nocturnal hemoglobinuria breakthrough," MacNeil, J.S., 44th Annual Meeting of the American Society of Hematology, Medscape Medical News, (Dec. 13, 2002); [online]; Medscape from WebMD; [Retrieved on Jun. 17, 2003. Retrieved from the world wide web at medscape.com/viewarticle/446336 XP009106338.

Merck Manual of Diagnosis and Therapy (The), Seventeenth Edition, Chapter 127 Anemias, 849-883 (1999).

Hillmen et al., "Eculizumab, a C5 Complement-Blocking Antibody, Controls Hemolysis in Paroxysmal Nocturnal Hemoglobinuria (PNH) with Responses Maintained over prolonged Period of Therapy" Journal of the American Society of Hematology, vol. 102(11), Abstract 1858 (2003).

Hillmen et al., "Eculizumab, a C5 complement-blocking antibody, controls haemolysis in paroxysmal nocturnal haemoglobinuria (PNH) with responses maintained over a prolonged period of therapy," British Journal of Haematology, vol. 125 (Suppl. 1): 1-72, Abstract 5 (2004).

U.S. Appl. No. 15/260,888, filed Apr. 11, 2017, J. Rogers.

U.S. Appl. No. 15/284,015, filed Apr. 11, 2017, J. Rogers.

Mortazavi et al., "The spectrum of PIG-A gene mutations in a plastic anemia/paroxysmal nocturnal hemoglobinuria (AAIPNH): a high incidence of multiple mutations and evidence of a mutational hot spot," Blood 101 2833-2841 (2003).

Moyo et al., "Natural history of paroxysmal nocturnal haemoglobinuria using modem diagnostic assays," British J Haematology 126, 133-138 (2004).

Notice of Opposition for EP Patent No. 1720571, dated Mar. 18, 2013.

Parker et al., Diagnosis and management of paroxysmal nocturnal hemoglobinuria, Blood, 106(12):3699-3709 (2005).

Paroxysmal nocturnal hemoglobinuria, included; PNH, included phosphatidylinositol glycan, class A, pseudogene 1, included; pigap1, included piga-related processed gene, included [online]. OM 1M-Online Medelian Inheritance in Man; John Hopkins University; [Retrieved on Jun. 18, 2003]. Retrieved from the world wide web at ncbi.nlm.nih.gov/entrez/query.fcgi?cmd=Retrieve&db=OMIM&dopt=detailed . . . .

Reiter et al., "Cell-free hemoglobin limits nitric oxide bioavailability in sickle-cell disease," Nature Medicine 8 (12):1383-1389 (2002).

Richards et al., "Evolution of GPI-Deficient Clones Predicts Clinical Course in Paroxysmal Nocturnal Haemoglobinuria," Blood, 104:Abstract 172 (2004).

Rodary et al., "Patient preference for either the EORTC QLQ-C30 or the FACIT Quality of Life (QOL) measures: a study performed in patient suffering from carcinoma of an unknown primary site (CUP)," European Journal of Cancer, vol. 40, pp. 521-528 (2004).

Rosse et al., Immune-mediated hemolytic anemia, Hematology Am Soc Hematol Educ. Program, 48-62 (2004) XP002497825.

Rother et al., Eculizumab, a C5 complement-blocking antibody, abolishes hemolysis and reduces transfusion dependency in patients with paroxysmal nocturnal hemoglobinuria (PNH), Molecular Immunology, vol. 40(2-4), p. 197; XP009163498, (2003).

Rother et al., The clinical sequelae of intravascular hemolysis and extracellular plasma hemoglobin, JAMA 293 (13):1653-1662 (2005).

Stebler et al., High-dose recombinant human erythropoietin for treatment of anemia in myelodysplastic syndromes and paroxysmal nocturnal hemoglobinuria: a pilot study, Exp. Hematol. 18:1204-1208 (1990).

Strauss et al. "Alternative pathway of complement in sickle cell disease," Pediat. Res., vol. 11:285-289 (1977).

Stuart et al., "Sickle-cell disease," Lancet, vol. 364:1343-60 (2004).

Tang and Pikal, Design of Freeze-Drying Processes for Pharmaceuticals: Practical Advice, Pharmaceutical Research, vol. 21 (2):191-200 (2004).

Thomas et al., Inhibition of complement activity by humanized anti-C5 antibody and single chain Fv, Mol.Imm. 33 (17-18):1389-1401, XP002262113 (1996).

Vakeva, et al., "Myocardial infarction and apoptosis after myocardial ischemia and reperfusion," Circulation 97:2259-2267 (1998).

\* cited by examiner

SEQUENCE LISTING

<160> NUMBER OF SEQ ID NOS: 10

<210> SEQ ID NO 1
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala
        115                 120

<210> SEQ ID NO 2
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Ser Asn Tyr
            20                  25                  30

Trp Ile Gln Trp Val Arg Gln Ala Pro Gly Gln Gly Leu Glu Trp Met
        35                  40                  45

Gly Glu Ile Leu Pro Gly Ser Gly Ser Thr Glu Tyr Thr Glu Asn Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Phe Phe Gly Ser Ser Pro Asn Trp Tyr Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

-continued

```
Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445
```

<210> SEQ ID NO 3
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Gly Ala Ser
        35                  40                  45

Glu Asn Ile Tyr Gly Ala Leu Asn Trp Tyr Gln Gln Lys Pro Gly Lys
    50                  55                  60

Ala Pro Lys Leu Leu Ile Tyr Gly Ala Thr Asn Leu Ala Asp Gly Val
65                  70                  75                  80
```

```
Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Asn
            100                 105                 110

Val Leu Asn Thr Pro Leu Thr Phe Gly Gln Gly Thr Lys Val Glu Ile
        115                 120                 125

Lys Arg Thr
    130

<210> SEQ ID NO 4
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
        35                  40                  45

Tyr Gly Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Asn Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Tyr Trp Ile Gln
1               5
```

```
<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Glu Ile Leu Pro Gly Ser Gly Ser Thr Glu Tyr Thr Glu Asn Phe Lys
1               5                   10                  15

Asp

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Phe Phe Gly Ser Ser Pro Asn Trp Tyr Phe Asp Val
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ala Ser Glu Asn Ile Tyr Gly Ala Leu Asn
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ala Thr Asn Leu Ala Asp
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Asn Val Leu Asn Thr Pro Leu Thr
1               5
```

TREATMENT OF PAROXYSMAL NOCTURNAL HEMOGLOBINURIA PATIENTS BY AN INHIBITOR OF COMPLEMENT

CROSS REFERENCE TO RELATED APPLICATIONS

This application is a continuation of U.S. patent application Ser. No. 13/426,973, filed Mar. 22, 2012, which is a continuation of U.S. patent application Ser. No. 12/225,040, filed on May 13, 2009, which is a 35 U.S.C. 371 national stage filing of International Application No. PCT/US2007/006606, filed Mar. 15, 2007. The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Feb. 13, 2017, is named AXJ_114BUSCN2_Seq _Listing.txt and is 10,244 bytes in size.

BACKGROUND

Paroxysmal nocturnal hemoglobinuria (PNH) is an acquired hematologic disease that results from clonal expansion of hematopoietic stem cells with somatic mutations in the X-linked gene called PIG-A.[1,2] Mutations in PIG-A lead to an early block in the synthesis of glycosylphosphatidylinositol (GPI)-anchors, which are required to tether many proteins to the cell surface. Consequently, PNH blood cells have a partial (type II) or complete (type III) deficiency of GPI-anchored proteins.

Intravascular hemolysis is a prominent feature of PNH and a direct result of the absence of the GPI-anchored complement regulatory protein CD59.[3,4] Under normal circumstances, CD59 blocks the formation of the terminal complement complex (also called the membrane attack complex) on the cell surface, thereby preventing erythrocyte lysis and platelet activation.[5-8] Excessive or persistent intravascular hemolysis in PNH patients not only results in anemia (normal ranges of hemoglobin are 14-18 g/dL for men and 12-16 g/dL for women, and persons with lower levels are considered to be anemic), but also heomoglobinuria and clinical sequelae related to the release of the erythrocyte contents into the circulation: fatigue, thrombosis, abdominal pain, dysphagia, erectile dysfunction, and pulmonary hypertension.[9,10,21,22] Indeed, impaired quality of life in PNH is disproportionate to the degree of anemia. Many PNH patients depend on blood transfusions to maintain adequate erythrocyte hemoglobin levels. There have been no therapies that effectively reduce intravascular hemolysis and improve the associated clinical morbidities in PNH.

Eculizumab is a humanized monoclonal antibody directed against the terminal complement protein C5.[11] In a preliminary, 12-week, open-label clinical study in 11 PNH patients, eculizumab was shown to reduce intravascular hemolysis and transfusion requirements.[12] However, this unblinded study involved a small number of patients with no control arm and without protocol-driven transfusion standards.

SUMMARY

The present pivotal, phase II study, Transfusion Reduction Efficacy and Safety Clinical Investigation, Randomized, Multi-Center, Double-Blind, Placebo-Controlled, Using Eculizumab in Paroxysmal Nocturnal Hemoglobinuria (TRIUMPH), evaluated the effect of eculizumab on the stabilization of hemoglobin levels and transfusion requirements during 6 months of treatment in a cohort of 87 transfusion-dependent PNH patients. Measures of intravascular hemolysis and quality of life were also assessed. This is the first placebo controlled study of a PNH patient population to control hemolysis and to differentiate between the effects due to hemolysis and the effects due to anemia.

It has been surprisingly discovered that certain aspects of quality of life were unexpectedly improved by the treatment of PNH patients with eculizumab. Furthermore, these improvements in the quality of life were independent of transfusion. The improved aspects include, e.g., global health status, physical functioning, emotional functioning, cognitive functioning, role functioning, social functioning, fatigue, pain, dyspnea, appetite loss and insomnia. Improvement was also seen in nausea and vomiting, diarrhea, constipation, and financial difficulties but did not reach the level of statistical significance. Because the treated patients remained anemic throughout their treatment, it was unexpected that all of these improvements would have been seen because they were previously thought to be a result of the patient being anemic. Although not wishing to be bound by any theory, it appears that some of the symptoms are likely due, at least in part, to hemolysis and release of hemoglobin into the bloodstream and do not result solely from the patient being anemic. The treatment with eculizumab decreases the amount of lysis thereby limiting hemoglobin release into the bloodstream, thereby apparently resulting in the improvements seen in the treated patients' quality of life. The results presented herein indicate that any treatment that decreases hemolysis in a patient will result in an improvement in the quality of life of said patient.

In certain aspects, the application provides a method to improve at least one aspect of the quality of life of a patient suffering from paroxysmal nocturnal hemoglobinuria, said method comprising administering to said patient in need thereof a compound which inhibits complement or inhibits formation of C5b-9.

In certain aspects, the application provides a method to improve at least one aspect of the quality of life of a patient suffering from paroxysmal nocturnal hemoglobinuria, said method comprising administering to said patient in need thereof a compound which inhibits intravascular hemolysis. In certain embodiments, said method results in a greater than 30% reduction in LDH in said patient.

In certain aspects, the application provides a method to improve at least one aspect of the quality of life of an anemic patient whose anemia results at least in part from hemolysis, said method comprising administering to said patient in need thereof a compound which inhibits intravascular hemolysis, wherein said patient remains anemic. In certain embodiments, said method results in a greater than 30% reduction in LDH in said patient.

In certain aspects, the application provides a method of prolonging the health-adjusted life expectancy of a patient comprising administering to said patient in need thereof a compound which inhibits formation of C5b-9. In certain embodiments, said patient is anemic. In certain embodiments, said patient remains anemic following treatment. In certain embodiments, said patient has a hemoglobin level less than i) 14 g/dL if a man or ii) 12 g/dL if a woman. In certain embodiments, said patient has a hemoglobin level less than i) 13 g/dL if a man or ii) 11 g/dL if a woman. In certain embodiments, said patient has a hemoglobin level less than i) 12 g/dL if a man or ii) 10 g/dL if a woman. In certain embodiments, said patient suffers from paroxysmal nocturnal hemoglobinuria.

In certain aspects, the application provides a pharmaceutical composition comprising an antibody that binds C5 or an active antibody fragment thereof. In certain embodiments, the antibody that binds C5 or an active antibody fragment thereof is eculizumab. In certain embodiments, the antibody that binds C5 or an active antibody fragment thereof is pexelizumab. In certain embodiments, the pharmaceutical formulations of the application may be administered to a subject, particularly a subject having PNH.

In certain aspects, the application provides a method of treating a patient suffering from paroxysmal nocturnal hemoglobinuria by administering a pharmaceutical composition comprising an antibody that binds C5 or an active antibody fragment thereof. In certain embodiments, the antibody that binds C5 or an active antibody fragment thereof is eculizumab. In certain embodiments, the antibody that binds C5 or an active antibody fragment thereof is pexelizumab. In certain embodiments, the pharmaceutical formulations of the application may be administered to a subject, particularly a subject having PNH.

In certain aspects, the application provides kits comprising a pharmaceutical composition of the application. In some embodiments, the kit further comprises at least one component of a closed sterile system. Components of the closed sterile system include, but are not limited to, needles, syringes, catheter based syringes, needle based injection devices, needle-less injection devices, filters, tubing, valves and cannulas. In a related embodiment, the kit comprise components for the removal of a preservative from the composition. Such components include filters, syringes, vials, containers, tubing, etc.

In certain embodiments, said quality of life is measured by a FACIT-Fatigue score. In certain embodiments, the FACIT-Fatigue score increases by at least 3 points. In certain embodiments, the FACIT-Fatigue score increases by ≥4 points.

In certain embodiments, said quality of life is measured by an EORTC QLQ-C30 score. In certain embodiments, said EORTC QLQ-C30 score improves by ≥10% of the pretreatment score. In certain embodiments, said aspect of the quality of life as measured by an EORTC QLQ-C30 score is selected from the group consisting of a) global health status, b) physical functioning, c) emotional functioning, d) cognitive functioning, e) role functioning, f) social functioning, g) fatigue, h) pain, i) dyspnea, j) appetite loss, and k) insomnia. In certain embodiments, said aspect of quality of life is fatigue.

In certain embodiments, said compound is selected from the group consisting of CR1, LEX-CR1, MCP, DAF, CD59, Factor H, cobra venom factor, FUT-175, complestatin, and K76 COOH. In certain embodiments, said compound is a steroid that suppresses complement.

In certain embodiments, said compound is selected from the group consisting of antibodies, active antibody fragments, soluble complement inhibitory compounds, proteins, soluble complement inhibitors with a lipid tail, protein fragments, peptides, small organic compounds, RNA aptamers, L-RNA aptamers, spiegelmers, antisense compounds, serine protease inhibitors, double stranded RNA, small interfering RNA, locked nucleic acid inhibitors, and peptide nucleic acid inhibitors. In certain embodiments, said compound is an antibody or an active antibody fragment. In certain embodiments, said antibody or active antibody fragment is selected from the group consisting of a) polyclonal antibodies, b) monoclonal antibodies, c) single chain antibodies, d) chimeric antibodies, e) humanized antibodies f) Fabs, g) F(ab')s, h) F(ab')$_2$s, i) Fvs, j) diabodies, and k) human antibodies.

In certain embodiments, said antibody or an active antibody fragment thereof binds C5. In certain embodiments, said antibody or active antibody fragment blocks C5 cleavage. In certain embodiments, said antibody or active antibody fragment inhibits the formation of C5b-9. In certain embodiments, said antibody is eculizumab. In certain embodiments, said antibody or active antibody fragment is administered for at least 6 months. In certain embodiments, said patient has aplastic anemia or myelodysplastic syndrome.

In certain embodiments, said antibody that binds C5 or an active antibody fragment thereof is administered in a single unit dosage form. In certain embodiments, the single unit dosage form is a 300 mg unit dosage form. In certain embodiments, the single unit dosage form is lyophilized. In certain embodiments, the single unit dosage form is a sterile solution. In certain embodiments, the single unit dosage form is a preservative free formulation. In certain embodiments, the 300 mg single-use dosage form comprises 30 ml of a 10 mg/ml sterile, preservative free solution.

In certain embodiments, the antibody that binds C5 or an active antibody fragment thereof comprises an altered constant region, wherein said antibody or antigen-binding fragment exhibits decreased effector function relative to an anti-CDCP1 antibody with a native constant region. In certain embodiments, decreased effector function comprises one or more properties of the following group: a) decreased antibody-dependent cell-mediated cytotoxicity (ADCC), and b) decreased complement dependent cytotoxicity (CDC), compared to an anti-CDCP1 antibody with a native constant region. In certain embodiments, the altered constant region comprises a G2/G4 construct in place of the G1 domain.

In certain embodiments, the antibody that binds C5 or an active antibody fragment thereof comprises a heavy chain variable region and a light chain variable region, wherein the heavy chain variable region comprises one or more CDR regions having an amino acid sequence selected from the group consisting of SEQ ID NO:5, SEQ ID NO:6, or SEQ ID NO:7, and wherein the light chain variable region comprises one or more CDR regions having an amino acid sequence selected from the group consisting of SEQ ID NO:8, SEQ ID NO:9, or SEQ ID NO:10. In certain embodiments, the antibody that binds C5 or an active antibody fragment thereof comprises a heavy chain variable region and a light chain variable region, wherein the heavy chain variable region consists of SEQ ID NO: 1 and the light chain variable region consists of SEQ ID NO: 3. In certain embodiments, the pharmaceutical composition comprises eculizumab. In certain embodiments, the pharmaceutical composition comprises pexelizumab. In certain embodiments, the antibody that binds C5 or an active antibody fragment thereof comprises a heavy chain and a light chain, wherein the heavy chain consists of SEQ ID NO: 2 and the light chain consists of SEQ ID NO: 4.

In certain embodiments, said patient is anemic. In certain embodiments, said patient remains anemic following treatment. In certain embodiments, said patient has a hemoglobin level less than i) 14 g/dL if a man or ii) 12 g/dL if a woman. In certain embodiments, said patient has a hemoglobin level less than i) 13 g/dL if a man or ii) 11 g/dL if a woman. In certain embodiments, said patient has a hemoglobin level less than i) 12 g/dL if a man or ii) 10 g/dL if a woman.

In certain embodiments, said health-adjusted life expectancy is measured according to a unit selected from the group consisting of Years of potential life lost, Disability-free life expectancy, Health-adjusted life year, Quality adjusted life year, Healthy years equivalents, Healthy days gained, Episode-free day, Q-TWiST, Health Utilities Index, or Years of healthy life.

In certain embodiments, the health-adjusted life expectancy in a subject is prolonged by at least one day. In certain embodiments, the health-adjusted life expectancy in a subject is prolonged by at least week. In certain embodiments, the health-adjusted life expectancy in a subject is prolonged by at least one month. In certain embodiments, the health-adjusted life expectancy in a subject is prolonged by at least one year.

In certain embodiments, the pharmaceutical composition is in a single unit dosage form. In certain embodiments, the single unit dosage form is a 300 mg unit dosage form. In certain embodiments, the pharmaceutical composition is lyophilized. In certain embodiments, the pharmaceutical composition is a sterile solution. In certain embodiments, the pharmaceutical composition is a preservative free formulation. In certain embodiments, the pharmaceutical composition comprises a 300 mg single-use formulation of 30 ml of a 10 mg/ml sterile, preservative free solution. In certain embodiments, the pharmaceutical composition comprises an antibody that binds C5 or an active antibody fragment thereof.

BRIEF DESCRIPTION OF THE FIGURES

FIG. 1A shows the degree of intravascular hemolysis in PNH patients, demonstrated by mean lactate dehydrogenase (LDH) levels. FIG. 1B shows the mean proportion of PNH type III erythrocytes assessed for placebo- and eculizumab-treated patients.

DETAILED DESCRIPTION

I. Definitions

Figure 1A:
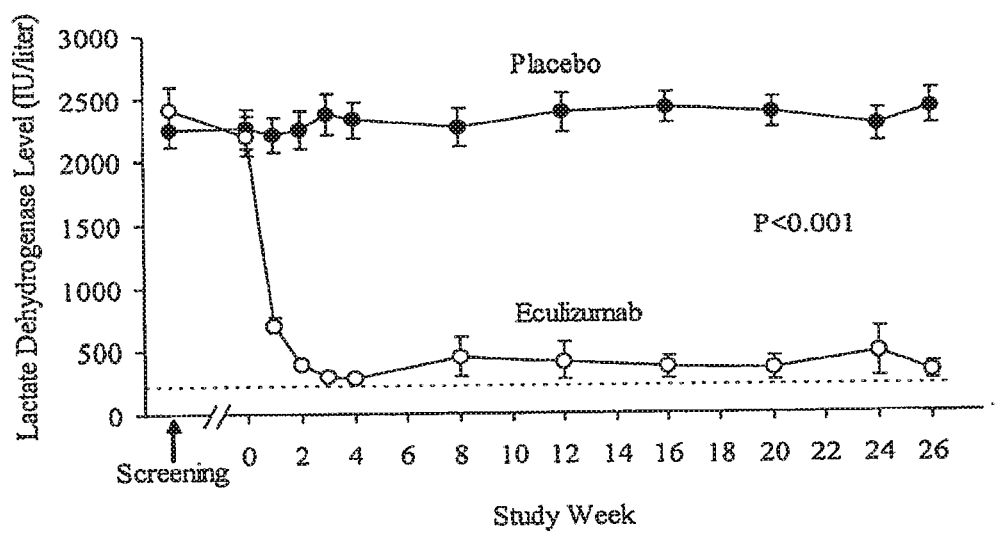
FIGS. 1A-B show that eculizumab treatment decreases intravascular hemolysis and increases PNH type III erythrocytes.

The term "derived from" means "obtained from" or "produced by" or "descending from".

The term "genetically altered antibodies" means antibodies wherein the amino acid sequence has been varied from that of a native antibody. Because of the relevance of recombinant DNA techniques to this application, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

The term "an antigen-binding fragment of an antibody" refers to any portion of an antibody that retains the binding utility to the antigen. An exemplary antigen-binding fragment of an antibody is the heavy chain and/or light chain CDR, or the heavy and/or light chain variable region.

The term "homologous," in the context of two nucleic acids or polypeptides refers to two or more sequences or subsequences that have at least about 85%, at least 90%, at least 95%, or higher nucleotide or amino acid residue identity, when compared and aligned for maximum correspondence, as measured using the following sequence comparison method and/or by visual inspection. In certain embodiments, the "homolog" exists over a region of the sequences that is about 50 residues in length, at least about 100 residues, at least about 150 residues, or over the full length of the two sequences to be compared.

Methods of determining percent identity are known in the art. "Percent (%) sequence identity" with respect to a specified subject sequence, or a specified portion thereof, may be defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. 215:403-410 (1997); http://blast.wustl.edu/blast/READMB.htm-1) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported.

II. Overview

The present disclosure relates to a method of treating paroxysmal nocturnal hemoglobinuria ("PNH"), more specifically to improving certain aspects of quality of life which are impaired in PNH patients, and other hemolytic diseases in mammals. Specifically, the methods of treating hemolytic diseases, which are described herein, involve using compounds which bind to or otherwise block the generation and/or activity of one or more complement components. The present methods have been found to provide surprising results. For instance, hemolysis rapidly ceases upon administration of the compound which binds to or otherwise blocks the generation and/or activity of one or more complement components, with hemoglobinuria being significantly reduced after treatment. Also, hemolytic patients can be rendered less dependent on transfusions or transfusion-independent for extended periods (twelve months or more), well beyond the 120 day life cycle of red blood cells. In addition, type III red blood cell count can be increased dramatically in the midst of other mechanisms of red blood cell lysis (non-complement mediated and/or earlier complement component mediated e.g., Cb3). Another example of a surprising result is that symptoms resolved, indicating that NO serum levels were increased enough even in the presence of other mechanisms of red blood cell lysis. These and other results reported herein are unexpected and could not be predicted from prior treatments of hemolytic diseases.

III The Complement System

The complement system, useful complement inhibitors, and use of these inhibitors to treat PNH and other patients are more fully described in PCT Patent Application PCT/US2005/003225 filed Feb. 3, 2005 and published as International Publication Number WO 2005/074607 A2 on Aug. 18, 2005, the contents of which are incorporated herein by reference in their entirety.

The complement system acts in conjunction with other immunological systems of the body to defend against intrusion of cellular and viral pathogens. There are at least 25 complement proteins, which are found as a complex collection of plasma proteins and membrane cofactors. The plasma proteins make up about 10% of the globulins in vertebrate serum. Complement components achieve their immune defensive functions by interacting in a series of intricate but precise enzymatic cleavage and membrane binding events. The resulting complement cascade leads to the production of products with opsonic, immunoregulatory, and lytic functions.

The complement cascade progresses via the classical pathway or the alternative pathway. These pathways share many components and, while they differ in their initial steps, they converge and share the same "terminal complement" components (C5 through C9) responsible for the activation and destruction of target cells.

The classical complement pathway is typically initiated by antibody recognition of and binding to an antigenic site on a target cell. The alternative pathway is usually antibody independent and can be initiated by certain molecules on pathogen surfaces. Both pathways converge at the point where complement component C3 is cleaved by an active protease (which is different in each pathway) to yield C3a and C3b. Other pathways activating complement attack can act later in the sequence of events leading to various aspects of complement function.

C3a is an anaphylatoxin. C3b binds to bacterial and other cells, as well as to certain viruses and immune complexes, and tags them for removal from the circulation. C3b in this role is known as opsonin. The opsonic function of C3b is considered to be the most important anti-infective action of the complement system. Patients with genetic lesions that block C3b function are prone to infection by a broad variety of pathogenic organisms, while patients with lesions later in the complement cascade sequence, i.e., patients with lesions that block C5 functions, are found to be more prone only to Neisseia infection, and then only somewhat more prone (Fearon, 1983).

C3b also forms a complex with other components unique to each pathway to form classical or alternative C5 convertase, which cleaves C5 into C5a and C5b. C3 is thus regarded as the central protein in the complement reaction sequence since it is essential to both the alternative and classical pathways (Wurzner et al., 1991). This property of C3b is regulated by the scrum protease Factor T, which acts on C3b to produce iC3b. While still functional as opsonin, iC3b cannot form an active C5 convertase.

C5 is a 190 kDa beta globulin found in normal serum at approximately 75 µg/mL (0.4 µM). C5 is glycosylated, with about 1.5-3 percent of its mass attributed to carbohydrate. Mature C5 is a heterodimer of a 999 amino acid 115 kDa alpha chain that is disulfide linked to a 656 amino acid 75 kDa beta chain. C5 is synthesized as a single chain precursor protein product of a single copy gene (Haviland et al., 1991). The cDNA sequence of the transcript of this gene predicts a secreted pro-C5 precursor of 1659 amino acids along with an 18 amino acid leader sequence.

The pro-C5 precursor is cleaved after amino acid 655 and 659, to yield the beta chain as an amino terminal fragment (amino acid residues +1 to 655) and the alpha chain as a carboxyl terminal fragment (amino acid residues 660 to 1658), with four amino acids deleted between the two.

C5a is cleaved from the alpha chain of C5 by either alternative or classical C5 convertase as an amino terminal fragment comprising the first 74 amino acids of the alpha chain (i.e., amino acid residues 660-733). Approximately 20 percent of the 11 kDa mass of C5a is attributed to carbohydrate. The cleavage site for convertase action is at or immediately adjacent to amino acid residue 733. A compound that would bind at or adjacent to this cleavage site would have the potential to block access of the C5 convertase enzymes to the cleavage site and thereby act as a complement inhibitor.

C5 can also be activated by means other than C5 convertase activity. Limited trypsin digestion (Minta and Man, 1977; Wetsel and Kolb, 1982) and acid treatment (Yamamoto and Gewurz, 1978; Vogt et al., 1989) can also cleave C5 and produce active C5b.

C5a is another anaphylatoxin. C5b combines with C6, C7, and C8 to form the C5b-8 complex at the surface of the target cell. Upon binding of several C9 molecules, the membrane attack complex (MAC, C5b-9, terminal complement complex-TCC) is formed. When sufficient numbers of MACs insert into target cell membranes the openings they create (MAC pores) mediate rapid osmotic lysis of the target cells. Lower, non-lytic concentrations of MACs can produce other effects. In particular, membrane insertion of small numbers of the C5b-9 complexes into endothelial cells and platelets can cause deleterious cell activation. In some cases activation may precede cell lysis.

As mentioned above, C3a and C5a are anaphylatoxins. These activated complement components can trigger mast cell degranulation, which releases histamine and other mediators of inflammation, resulting in smooth muscle contraction, increased vascular permeability, leukocyte activation, and other inflammatory phenomena including cellular proliferation resulting in hypercellularity. C5a also functions as a chemotactic peptide that serves to attract pro-inflammatory granulocytes to the site of complement activation.

The beneficial effect of anti-C5 mAb has previously been reported in several experimental models including myocardial reperfusion (Vakeva at al., 1998), systemic lupus erythematosus (Wang et al., 1996) and rheumatoid arthritis (Wang et al., 1995); as well as in human clinical trials (Kirschfink, 2001) of autoimmune disease, cardiopulmonary bypass and acute myocardial infarction.

IV Measurer of Quality of Life

Various measurements exist to assess quality of life and the effect of medical interventions on quality of life for example the Mini-Mental State Examination (MMSE), the Short Test of Mental Status, the European Organization for Research and Treatment of Cancer (EORTC) Quality of Life Questionnaire, the FACIT questionnaires and subscales including fatigue and anemia, the Likert Scale, and Borg Scale (Tombaugh, et al., J. Am. Geriatr. Soc. 40:922, 1992; Cummings, JAMA. 269(18):2420, 1993; Crum, et al., JAMA. 269(18):2386, 1993; Folstein, at al., J. Psychiat. Res. 12:189, 1975; Kokmen, et al., Mayo Clin. Proc. 62:281, 1987; Tang-Wai, et al., Arch. Neurol. 60:1777, 2003; Tamburini, Ann. Oncol. 12(Suppl. 3):S7, 2001; Webster et al., Health and Quality of Life Outcomes. 1:79, 2003, www.hqlo.com/content/I/I/79; Grant, et al., Chest. 116: 1208, 1999; and www.qolid.org). Any of these measurements may be used to assess the change in quality of life due to administration of a compound which inhibits complement or inhibits formation of C5b-9.

In certain embodiments, improvement in quality of life due to administration of a compound which inhibits complement or inhibits formation of C5b-9 is measured by the Functional Assessment of Chronic Illness Therapy (FACIT) Measurement System. In certain embodiments, improvement in quality of life is measured by: a) full scales; b) stand-alone subscales; and c) symptom indices.

In certain embodiments, improvement in quality of life due to administration of a compound which inhibits complement or inhibits formation of C5b-9 is measured by a European Organization for Research and Treatment of Cancer (EORTC) Quality of Life Questionnaire. In certain embodiments, the EORTC questionnaire is the QLQ-C30.

In certain embodiments, improvement in quality of life is measured by the health-adjusted life expectancy (HALE) index as described in Wilkins, R. and Adams, O B., Am J Public Health, 73:1073-1080 (1983). Health-adjusted life expectancy is an average of the quality-adjusted life years (QALY) for a given population and can be used to evaluate the therapeutic value of a medical intervention. Quality-adjusted life years is a health index that weighs each year of life on a scale from 1 to 0 (Weinstein M C and Stason W B, N Engl J Med, 296:716-721 (1977)). Perfect health is rated as 1, death is rated as 0, and disability and pain are rated based on severity. QALY is determined by multiplying the number of years at each health status.

In certain embodiments, improvement in quality of life is measured by the following instruments: Years of potential life lost, Disability-free life expectancy, Health-adjusted life year, Quality adjusted life year, Healthy years equivalents, Healthy days gained, Episode-free day, Q-TWiST, Health Utilities Index, and Years of healthy life. These measurements account for both changes in mortality as well as changes in morbidity and disability. Any of these measurements may be used to assess the change in quality of life due to administration of a compound which inhibits complement or inhibits formation of C5b-9.

In one embodiment, the disclosed methods improve the quality of life of a patient for at least one day, at least one week, at least two weeks, at least three weeks, at least one month, at least two months, at least three months, at least 6 months, at least one year, at least 18 months, at least two years, at least 30 months, or at least three years, or the duration of treatment.

In certain embodiments, the symptoms used to measure quality of if are scaled for intensity. In certain embodiments, the symptoms are scaled for frequency. In certain embodiments, the symptoms are scaled for intensity and frequency.

In certain aspects, the application provides a method for prolonging the health-adjusted life expectancy of a subject comprising administering to the subject a compound which inhibits complement or inhibits formation of C5b-9. The above measurements account for both changes in mortality as well as changes in morbidity and disability. Any of these measurements may be used to assess the change in quality-adjusted life expectancy due to administration of a compound which inhibits complement or inhibits formation of C5b-9.

In one embodiment, the disclosed methods prolong the health-adjusted life expectancy in a subject by at least one day, at least one week, at least two weeks, at least three weeks, at least one month, at least two months, at least three months, at least 6 months, at least one year, at least 18 months, at least two years, at least 30 months, or at least three years as measured by the health-adjusted life expectancy (HALE) index as described in Wilkins et al. Am J Public Health, 73:1073-1080 (1983). Health-adjusted life expectancy is an average of the quality-adjusted life years (QALY) for a given population and can be used to evaluate the therapeutic value of a medical intervention. Quality-adjusted life years is a health index that weighs each year of life on a scale from 1 to 0 (Weinstein et al., N Engl J Med, 296:716-721 (1977)). Perfect health is rated as 1, death is rated as 0, and disability and pain are rated based on severity. QALY is determined by multiplying the number of years at each health status.

V Inhibitors of the Complement Cascade

In certain embodiments, any compound which binds to or otherwise blocks the generation and/or activity of one or more complement components can be used in the present methods. In certain embodiments, a complement inhibitor may be a small molecule (up to 6,000 Da in molecular weight), a nucleic acid or nucleic acid analog, a peptidomimetic, or a macromolecule that is not a nucleic acid, a serine protease inhibitor, or a protein. These agents include, but are not limited to, small organic molecules, RNA aptamers including ARC187 (which is commercially available from Archemix Corp., Cambridge, Mass.), L-RNA aptamers, Spiegelmers, antisense compounds, molecules which may be utilized in RNA interference (RNAI) such as double stranded RNA including small interfering RNA (siRNA), locked nucleic acid (LNA) inhibitors, peptide nucleic acid (PNA) inhibitors.

In certain embodiments, a complement inhibitor may be a protein or protein fragment. Proteins are known which inhibit the complement cascade, including CD59, CD55, CD46 and other inhibitors of C8 and C9 (see, e.g., U.S. Pat. No. 6,100,443). Proteins known as complement receptors and which bind complement are also known (see, Published PCT Patent Application WO 92/10205 and U.S. Pat. No. 6,057,131). Use of soluble forms of complement receptors, e.g., soluble CR1, can inhibit the consequences of complement activation such as neutrophil oxidative burst, complement mediated neural injury, and C3a and C5a production. In certain embodiments, a complement inhibitor may be naturally occurring or soluble forms of complement inhibitory compounds such as CR1, LEX-CR1, MCP, DAF, CD59, Factor H, cobra venom factor, FUT-175, complestatin, and K76 COOH. Those of skill in the art recognize the above as some, but not all, of the known methods of inhibiting complement and its activation.

In certain embodiments, a complement inhibitor may be an antibody capable of inhibiting complement, such as an antibody that can block the formation of MAC. For example, an antibody complement inhibitor may include an antibody that binds C5. Such anti-C5 Antibodies may directly interact with C5 and/or C5b, so as to inhibit the formation of and/or physiologic function of C5b.

Suitable anti-C5 antibodies are known to those of skill in the art. Antibodies can be made to individual components of activated complement, e.g., antibodies to C7, C9, etc. (see, e.g., U.S. Pat. No. 6,534,058; published U.S. patent application US 2003/0129187; and U.S. Pat. No. 5,660,825). U.S. Pat. No. 6,355,245 teaches an antibody which binds to C5 and inhibits cleavage into C5a and C5b thereby decreasing the formation not only of C5a but also the downstream complement components.

The concentration and/or physiologic activity of C5a and C5b in a body fluid can be measured by methods well known in the art. For C5a such methods include chemotaxis assays, RIAs, or ELISAs (see, for example, Ward and Zvaifler, J Clin Invest. 1971 March; 50(3):606-16; Wurzner, et al., Complement Inflamm. 8:328-340, 1991). For C5b, hemolytic assays or assays for soluble C5b-9 as discussed herein can be used. Other assays known in the art can also be used. Using assays of these or other suitable types, candidate antibodies capable of inhibiting complement such as anti-C5 antibodies, now known or subsequently identified, can be screened in order to 1) identify compounds that are useful in the practice of the application and 2) determine the appropriate dosage levels of such compounds.

An antibody capable of inhibiting complement such as an antibody that binds C5 affecting C5b is preferably used at concentrations providing substantial reduction (i.e., reduction by at least about 25% as compared to that in the absence of the antibody that binds C5) in the C5b levels present in at least one blood-derived fluid of the patient following activation of complement within the fluid. Such concentrations can be conveniently determined by measuring the cell-lysing ability (e.g., hemolytic activity) of complement present in the fluid or the levels of soluble C5b-9 present in the fluid. Accordingly, a specific concentration for an antibody that affects C5b is one that results in a substantial reduction (i.e., a reduction by at least about 25%) in the cell-lysing ability of the complement present in at least one of the patient's blood-derived fluids. Reductions of the cell-lysing ability of complement present in the patient's body fluids can be measured by methods well known in the art such as, for example, by a conventional hemolytic assay such as the hemolysis assay described by Kabat and Mayer (eds), "Experimental Immunochemistry, 2d Edition", 135-240, Springfield, Ill., CC Thomas (1961), pages 135-139, or a conventional variation of that assay such as the chicken erythrocyte hemolysis method described below.

Specific antibodies capable of inhibiting complement, such as an antibody that binds C5, are relatively specific and do not block the functions of early complement components. In particular, such specific agents will not substantially impair the opsonization functions associated with complement component C3b, which functions provide a means for clearance of foreign particles and substances from the body.

C3b is generated by the cleavage of C3, which is carried out by classical and/or alternative C3 convertases and results in the generation of both C3a and C3b. Therefore, in order not to impair the opsonization functions associated with C3b, specific antibodies capable of inhibiting complement such as an antibody that binds C5 do not substantially interfere with the cleavage of complement component C3 in a body fluid of the patient (e.g., serum) into C3a and C3b. Such interference with the cleavage of C3 can be detected by measuring body fluid levels of C3a and/or C3b, which are produced in equimolar ratios by the actions of the C3 convertases. Such measurements are informative because C3a and C3b levels will be reduced (compared to a matched sample without the antibody capable of inhibiting complement such as an antibody that binds C5) if cleavage is interfered with by an antibody capable of inhibiting complement such as an antibody that binds C5.

In practice, the quantitative measurement of such cleavage is generally more accurate when carried out by the measurement of body fluid C3a levels rather than of body fluid C3b levels, since C3a remains in the fluid phase whereas C3b is rapidly cleared. C3a levels in a body fluid can be measured by methods well known in the art such as, for example, by using a commercially available C3a EIA kit, e.g., that sold by Quidel Corporation, San Diego, Calif., according to the manufacturer's specifications. Particularly specific antibodies capable of inhibiting complement such as an antibody that binds C5 produce essentially no reduction in body fluid C3a levels following complement activation when tested in such assays.

Certain antibodies of the disclosure will prevent the cleavage of C5 to form C5a and C5b, thus preventing the generation of the anaphylatoxic activity associated with C5a and preventing the assembly of the membrane attack complex associated with C5b. As discussed above, in a particular embodiment, these anti-C5 antibodies will not impair the opsonization function associated with the action of C3b.

A preferred method of inhibiting complement activity is to use a monoclonal antibody which binds to complement C5 and inhibits cleavage. This decreases the formation of both C5a and C5b while at the same time allowing the formation of C3a and C3b which are beneficial to the recipient. Such antibodies which are specific to human complement are known (U.S. Pat. No. 6,355,245). These antibodies disclosed in U.S. Pat. No. 6,355,245 include a preferred whole antibody (now named eculizumab). A similar antibody against mouse C5 is called BB5.1 (Frei at al., Mol. Cell. Probes. 1:141-149 (1987)). Antibodies to inhibit complement activity need not be monoclonal antibodies. They can be, e.g., polyclonal antibodies. They may additionally be antibody fragments. An antibody fragment includes, but is not limited to, an Fab, F(ab'), F(ab')$_2$, single-chain antibody, and Fv. Furthermore, it is well known by those of skill in the art that antibodies can be humanized (Jones at al., Nature 321:522-5 (1986)), chimerized, or deimmunized. The antibodies to be used in the present disclosure may be any of these. It is preferable to use humanized antibodies.

In specific embodiments, a therapeutic agent of the disclosure comprises an antibody or antibody fragment. Antibodies and fragments thereof may be made by any conventional method, such as those methods described herein. Antibodies are found in multiple forms, e.g., IgA, IgG, IgM, etc. Additionally, antibodies can be engineered in numerous ways. They can be made as single-chain antibodies (including small modular immunopharmaccticals or SMIPs™), Fab and F(ab')$_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203.

This invention provides fragments of anti-C5 antibodies, which may comprise a portion of an intact antibody, preferably the antigen-binding or variable region of the intact antibody. Examples of antibody fragments include Fab, Fab', F(ab')$_2$, and Fv fragments; diabodies; linear antibodies (Zapata et al., Protein Eng. 8:1057-1062 (1995)); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment of an antibody yields an F(ab')$_2$ fragment that has two antigen-combining sites and is still capable of cross-linking antigen.

"Fv" refers to the minimum antibody fragment that contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although likely at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them. Other chemical couplings of antibody fragments are also known.

"Single-chain Fv" or "scFv" antibody fragments comprise the $V_H$ and $V_L$ domains of an antibody, wherein these domains are present in a single polypeptide chain. Preferably, the Fv polypeptide further comprises a polypeptide linker between the $V_H$ and $V_L$ domains that enables the scFv to form the desired structure for antigen binding. For a review of scFv see Pluckthun in *The Pharmacology of Monoclonal Antibodies*, vol. 113, Rosenburg and Moore, eds. (Springer-Verlag: New York, 1994), pp. 269-315.

SMIPs are a class of single-chain peptide engineered to include a target binding region, effector domain (CH2 and CH3 domains). See, e.g., U.S. Patent Application Publication No. 20050238646. The target binding region may be derived from the variable region or CDRs of an antibody, e.g., an antibody that binds C5 of the application. Alternatively, the target binding region is derived from a protein that binds C5.

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger at al., Proc. Natl. Acad. Sci. USA, 90: 6444-6448 (1993).

It is well known that the binding to a molecule (or a pathogen) of antibodies with an Fc region assists in the processing and clearance of the molecule (or pathogen). The Fc portions of antibodies are recognized by specialized receptors expressed by immune effector cells. The Fc portions of IgG1 and IgG3 antibodies are recognized by Fc receptors present on the surface of phagocytic cells such as macrophages and neutrophils, which can thereby bind and engulf the molecules or pathogens coated with antibodies of these isotypes (C. A. Janeway at al., *Immunobiology* 5th edition, page 147, Garland Publishing (New York, 2001)).

This disclosure also provides monoclonal anti-C5 antibodies. A monoclonal antibody can be obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. In addition to their specificity, the monoclonal antibodies are advantageous in that they are often synthesized by the hybridoma culture, uncontaminated by other immunoglobulins. Monoclonal antibodies may also be produced in transfected cells, such as CHO cells and NS0 cells. The modifier "monoclonal" indicates the character of the antibody as being obtained from a substantially homogeneous population of antibodies and does not require production of the antibody by any particular method. For example, the monoclonal antibodies to be used in accordance with the present disclosure may be made by the hybridoma method first described by Kohler et al., Nature 256:495-497 (1975), or may be made by recombinant DNA methods (see. e.g., U.S. Pat. Nos. 4,816,567 and 6,331,415). The "monoclonal antibodies" may also be isolated from phage antibody libraries using the techniques described in Clackson et al., Nature 352:624-628 (1991) and Marks et al., J. Mol. Biol. 222:581-597 (1991), for example.

A description of the preparation of a mouse anti-human-C5 monoclonal antibody with specific binding characteristics is presented in U.S. Patent Application Publication No. 20050226870. Wurzner et al., Complement Inflamm. 8:328-340 (1991), describe the preparation of other mouse anti-human-C5 monoclonal antibodies referred to as N19-8 and N20-9.

Other antibodies specifically contemplated are "oligoclonal" antibodies. As used herein, the term "oligoclonal" antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule (e.g., C5). In view of the assays and epitopes disclosed herein, those skilled in the art can generate or select antibodies or mixtures of antibodies that are applicable for an intended purpose and desired need.

In certain embodiments that include a humanized and/or chimeric antibody, one or more of the CDRs are derived from an anti-human C5 antibody. In a specific embodiment, all of the CDRs are derived from an anti-human C5 antibody. In another specific embodiment, the CDRs from more than one anti-human C5 antibody are mixed and matched in a chimeric antibody. For instance, a chimeric antibody may comprise a CDR1 from the light chain of a first anti-human C5 antibody combined with CDR2 and CDR3 from the light chain of a second anti-human C5 antibody, and the CDRs from the heavy chain may be derived from a third anti-human C5 antibody. Further, the framework regions may be derived from one of the same anti-human C5 antibodies, from one or more different antibodies, such as a human antibody, or from a humanized antibody. Human or humanized antibodies are specific for administration to human patients.

In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared, as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology 10:1455-1460 (1992), regarding primatized antibody. See, e.g., Ladner at al., U.S. Pat. No. 4,946,778; and Bird et al., Science 242:423-426 (1988), regarding single chain antibodies.

In addition, functional fragments of antibodies, including fragments of chimeric, humanized, primatized or single chain antibodies, can also be produced. Functional fragments of the subject antibodies retain at least one binding function and/or modulation function of the fill-length antibody from which they are derived. Preferred functional fragments retain an antigen-binding function of a corresponding full-length antibody (such as for example, ability of antibody that binds C5 to bind C5).

General methods for the immunization of animals (in this case with C5 and/or C5b, etc.), isolation of antibody producing cells, fusion of such cells with immortal cells (e.g., myeloma cells) to generate hybridomas secreting monoclonal antibodies, screening of hybridoma supernatants for reactivity of secreted monoclonal antibodies with a desired antigen (in this case the immunogen or a molecule containing the immunogen), the preparation of quantities of such antibodies in hybridoma supernatants or ascites fluids, and for the purification and storage of such monoclonal antibodies, can be found in numerous publications. These include: Coligan, et al., eds. *Current Protocols In Immunology*, John Wiley & Sons, New York, 1992; Harlow and Lane, *Antibodies, A Laboratory Manual*, Cold Spring Harbor Laboratory, New York, 1988; Liddell and Cryer, *A Practical Guide To Monoclonal Antibodies*, John Wiley & Sons, Chichester, West Sussex, England, 1991; Montz at al., Cellular Immunol. 127:337-351 (1990); Wurzner at al., Complement Inflamm. 8:328-340 (1991); and Mollnes at al., Scand. J. Immunol. 28:307-312 (1988).

VI Method of Treatment

Methods of the application may be used to treat paroxysmal nocturnal hemoglobinuria associated symptoms. Methods of the application may be used to treat anemia associated symptoms. Treatment of paroxysmal nocturnal hemoglobinuria and/or anemia may be administered by standard means. Treatments of the application may be used in combination with other treatments of the application or known treatments for paroxysmal nocturnal hemoglobinuria and/or anemia. Treatments of the application may be co-administered with other treatments that treat symptoms of paroxysmal nocturnal hemoglobinuria and/or anemia.

VII Pharmaceutical Formulations and Uses

Methods of administration of small molecules, proteins, and nucleic acids are well-known to those of skill in the art. Methods of administration of antibodies are well-known to those of skill in the art. To achieve the desired inhibition, the antibodies can be administered in a variety of unit dosage forms. The dose will vary according to the particular antibody. For example, different antibodies may have different masses and/or affinities, and thus require different dosage levels. Antibodies prepared as Fab fragments will also require differing dosages than the equivalent intact immunoglobulins, as they are of considerably smaller mass than intact immunoglobulins, and thus require lower dosages to reach the same molar levels in the patient's blood. The dose will also vary depending on the manner of administration, the particular symptoms of the patient being treated, the overall health, condition, size, and age of the patient, and the judgment of the prescribing physician. Dosage levels of the antibodies for human subjects are generally between about 1 mg pet kg and about 100 mg per kg per patient per treatment, and preferably between about 5 mg per kg and about 50 mg per kg per patient per treatment. In terms of plasma concentrations, the antibody concentrations are preferably in the range from about 25 µg/mL to about 500 µg/mL. However, greater amounts may be required for extreme cases and smaller amounts may be sufficient for milder cases.

In certain embodiments, the pharmaceutical composition is in a single unit dosage form. In certain embodiments, the single unit dosage form is a 300 mg unit dosage form. In certain embodiments, the pharmaceutical composition is lyophilized. In certain embodiments, the pharmaceutical composition is a sterile solution. In certain embodiments, the pharmaceutical composition is a preservative free formulation. In certain embodiments, the pharmaceutical composition comprises a 300 mg single-use formulation of 30 ml of a 10 mg/ml sterile, preservative free solution. In certain embodiments, the antibody is administered according to the following protocol: 600 mg via 25 to 45 minute IV infusion every 7±2 days for the first 4 weeks, followed by 900 mg for the fifth dose 7±2 days later, then 900 mg every 14±2 days thereafter. Antibody is administered via IV infusion over 25 to 45 minute.

Administration of the anti-C5 antibodies will generally be performed by an intravascular route, e.g., via intravenous infusion by injection. Other routes of administration may be used if desired but an intravenous route will be the most preferable. Formulations suitable for injection are found in Remington's Pharmaceutical Sciences, Mack Publishing Company, Philadelphia, Pa., 17th ed. (1985). Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, and the like. In certain embodiments, complement inhibitors such as eculizumab may be administered via IV infusion and diluted to a final concentration of 5 mg/ml prior to administration.

Administration of the antibodies capable of inhibiting complement such as an antibody that binds C5 will generally be performed by a parenteral route, typically via injection such as intra-articular or intravascular injection (e.g., intravenous infusion) or intramuscular injection. Other routes of administration, e.g., oral (p.o.), may be used if desired and practicable for the particular antibody capable of inhibiting complement to be administered. Antibodies capable of inhibiting complement such as an antibody that binds C5 can also be administered in a variety of unit dosage forms and their dosages will also vary with the size, potency, and in vivo half-life of the particular antibody capable of inhibiting complement being administered. Doses of antibodies capable of inhibiting complement such as an antibody that binds C5 will also vary depending on the manner of administration, the particular symptoms of the patient being treated, the overall health, condition, size, and age of the patient, and the judgment of the prescribing physician.

In certain embodiments, a typical therapeutic treatment includes a series of doses, which will usually be administered concurrently with the monitoring of clinical endpoints with the dosage levels adjusted as needed to achieve the desired clinical outcome. In certain embodiments, treatment is administered in multiple dosages over at least a week. In certain embodiments, treatment is administered in multiple dosages over at least a month. In certain embodiments, treatment is administered in multiple dosages over at least a year. In certain embodiments, treatment is administered in multiple dosages over the remainder of the patient's life.

The frequency of administration may also be adjusted according to various parameters. These include the clinical response, the plasma half-life of the therapeutic of the disclosure, and the levels of the antibody in a body fluid, such as, blood, plasma, serum, or synovial fluid. To guide adjustment of the frequency of administration, levels of the therapeutic of the disclosure in the body fluid may be monitored during the course of treatment.

In certain embodiments, the frequency of administration may be adjusted according to an assay measuring cell-lysing ability of complement present in one or more of the patient's body fluids. The cell-lysing ability can be measured as percent hemolysis in hemolytic assays of the types described herein. A 10% or 25% or 50% reduction in the cell-lysing ability of complement present in a body fluid after treatment with the antibody capable of inhibiting complement used in the practice of the application means that the percent hemolysis after treatment is 90, 75, or 50 percent, respectively, of the percent hemolysis before treatment.

For the treatment of hemolytic diseases such as PNH by systemic administration of an antibody capable of inhibiting complement such as an antibody that binds C5 (as opposed to local administration), administration of a large initial dose is specific, i.e., a single initial dose sufficient to yield a substantial reduction, and more preferably an at least about 50% reduction, in the hemolytic activity of the patient's serum. Such a large initial dose is preferably followed by regularly repeated administration of tapered doses as needed to maintain substantial reductions of serum hemolytic titer. In another embodiment, the initial dose is given by both local and systemic routes, followed by repeated systemic administration of tapered doses as described above.

Formulations particularly useful for antibody-based therapeutic agents are also described in U.S. Patent App. Publication Nos. 20030202972, 20040091490 and 20050158316. In certain embodiments, the liquid formulations of the application are substantially free of surfactant and/or inorganic salts. In another specific embodiment, the liquid formulations have a pH ranging from about 5.0 to about 7.0. In yet another specific embodiment, the liquid formulations comprise histidine at a concentration ranging from about 1 mM to about 100 mM. In still another specific embodiment, the liquid formulations comprise histidine at a concentration ranging from 1 mM to 100 mM. It is also contemplated that the liquid formulations may further comprise one or more excipients such as a saccharide, an amino acid (e.g., arginine, lysine, and methionine) and a polyol. Additional descriptions and methods of preparing and analyzing liquid formulations can be found, for example, in PCT publications WO 03/106644, WO 04/066957, and WO 04/091658.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the pharmaceutical compositions of the application.

In certain embodiments, formulations of the subject antibodies are pyrogen-free formulations which are substantially free of endotoxins and/or related pyrogenic substances. Endotoxins include toxins that are confined inside microorganisms and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1): 223 (2000)). When therapeutic proteins are administered in amounts of several hundred or thousand milligrams per kilogram body weight, as can be the case with monoclonal antibodies, it is advantageous to remove even trace amounts of endotoxin.

Formulations of the subject antibodies include those suitable for oral, dietary, topical, parenteral (e.g., intravenous, intraarterial, intramuscular, subcutaneous injection), ophthalmologic (e.g., topical or intraocular), inhalation (e.g., intrabronchial, intranasal or oral inhalation, intranasal drops), rectal, and/or intravaginal administration. Other suitable methods of administration can also include rechargeable or biodegradable devices and controlled release polymeric devices. Stents, in particular, may be coated with a controlled release polymer mixed with an agent of the application. The pharmaceutical compositions of this disclosure can also be administered as part of a combinatorial therapy with other agents (either in the same formulation or in a separate formulation).

The amount of the formulation which will be therapeutically effective can be determined by standard clinical techniques. In addition, in vitro assays may optionally be employed to help identify optimal dosage ranges. The precise dose to be employed in the formulation will also depend on the route of administration, aid the seriousness of the disease or disorder, and should be decided according to the judgment of the practitioner and each patient's circumstances. Effective doses may be extrapolated from dose-response curves derived from in vitro or animal model test systems. The dosage of the compositions to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. For example, the actual patient body weight may be used to calculate the dose of the formulations in milliliters (mL) to be administered. There may be no downward adjustment to "ideal" weight. In such a situation, an appropriate dose may be calculated by the following formula: Dose (mL)=[patient weight (kg)×dose level (mg/kg)/drug concentration (mg/mL)]

To achieve the desired treatment results, anti-C5 antibodies can be administered in a variety of unit dosage forms. The dose will vary according to the particular antibody. For example, different antibodies may have different masses and/or affinities, and thus require different dosage levels. Antibodies prepared as Fab' fragments or single chain antibodies will also require differing dosages than the equivalent native immunoglobulins, as they are of considerably smaller mass than native immunoglobulins, and thus require lower dosages to reach the same molar levels in the patient's blood.

Other therapeutics of the disclosure can also be administered in a variety of unit dosage forms and their dosages will also vary with the size, potency, and in vivo half-life of the particular therapeutic being administered.

Doses of therapeutics of the disclosure will also vary depending on the manner of administration, the particular symptoms of the patient being treated, the overall health, condition, size, and age of the patient, and the judgment of the prescribing physician.

The formulations of the application can be distributed as articles of manufacture comprising packaging material and a pharmaceutical agent which comprises the antibody capable of inhibiting complement and a pharmaceutically acceptable carrier as appropriate to the mode of administration. The packaging material may include a label which indicates that the formulation is for use in the treatment of hemolytic diseases such as PNH. Although antibodies are preferred, especially anti-C5 antibodies which have already been shown to be safe and effective at decreasing the accumulation of downstream complement components in persons, the use of other complement inhibitors is also contemplated by this disclosure. The pharmaceutical formulations and uses of the disclosure may be combined with any known complement inhibitors or hemolytic diseases treatments known in the art.

In certain aspects, the application provides kits comprising a pharmaceutical composition of the application. In some embodiments, the kit farther comprises at least one component of a closed sterile system. Components of the closed sterile system include, but are not limited to, needles, syringes, catheter based syringes, needle based injection devices, needle-lees injection devices, filters, tubing, valves and cannulas. In a related embodiment, the kit comprise components for the removal of a preservative from the composition. Such components include filters, syringes, vials, containers, tubing, etc.

EXEMPLIFICATION

Methods
Patient Selection

The TRIUMPH trial consisted of a 2-week screening period, an observation period of up to 3 months duration, and a 26-week treatment period.

During the screening period, patients were evaluated with respect to inclusion and exclusion criteria. Men and women, 18 years or older, diagnosed as having PNH with a type III erythrocyte population of ≥10%, and who had received at least 4 transfusions in the previous 12 months were eligible. Concomitant administration of erythropoietin, immunosuppressants, corticosteroids, coumadin, low molecular weight heparin, iron supplements, and folic acid were not reasons for exclusion, provided the doses were steady prior to the first visit and throughout the duration of the study. Because of the increased frequency of neisserial infections in individuals genetically deficient in terminal complement proteins, all patients were vaccinated against Neisseria meningitides. Patients were to avoid conception. The protocol was approved by an Investigational Review Board at each clinical site and written informed consent was obtained from all patients enrolled.

Patients transfused with a mean pre-transfusion hemoglobin level>10.5 g/dL over the previous 12 months, and those who showed evidence of having a suppressed immune response, complement deficiency, or active bacterial infection, including any history of meningoooccal disease, were excluded from the study. Patients were also not eligible if they had previously received a bone marrow transplant or if they had participated in another trial or received another investigational drug within 30 days of the first visit. An individualized transfusion algorithm was calculated for each patient based on their prior-12-month transfusion history; the written algorithm documented the number of packed red blood cell (PRBC) units transfused for given hemoglobin values and served as a prospectively determined guide for transfusion during observation and treatment periods.

Each patient considered eligible entered an observation period of up to 13 weeks in order to confirm their PBRC transfusion dependence. At least one transfusion—termed the "qualifying" transfusion—during the 13-week observation period at a hemoglobin value at or below 9 g/dL with symptoms, or at or below 7 g/dL with or without symptoms, in accordance with the transfusion algorithm indicated for each patient, was a requirement to proceed to randomization. The hemoglobin value at which each individual's qualifying transfusion was administered, was defined as the hemoglobin "set point" for that individual for the purpose of the primary efficacy variable. A platelet count ≥100,000/mL and a LDH level≥11.5 times the upper limit of the normal range were also required either at screening or during the observation period for eligibility.

Study Design

Patients were randomly assigned on a one-on-one basis to receive either placebo or eculizumab (Soliris™, Alexion Pharmaceuticals, Inc.) within 10 days of the qualifying transfusion. Study medication was dosed in a blinded fashion as follows: 600 mg eculizumab for patients randomly assigned to active drug, or placebo for those patients randomly assigned to placebo, respectively via IV infusion every 7±1 days for 4 doses; followed by 900 mg eculizumab, or placebo, respectively, via IV infusion 7±1 day later; followed by a maintenance dose of 900 mg eculizumab, or placebo, respectively, via IV infusion every 14±2 days for a total of 26 weeks of treatment.

Measures of Clinical Efficacy

There were two co-primary endpoints in the study: (1) stabilization of hemoglobin levels, defined as a hemoglobin value maintained above the individual hemoglobin set point in the absence of transfusions for the entire 26-week treatment period, and (2) reduction in units of PRBCs transfused during the 26-week treatment phase of the study. The trigger for transfusion during the study period remained unchanged for each patient, as compared with their care before entry into the study: patients received blood transfusions when they had symptoms resulting from anemia and reached their individualized, predetermined "set point". Pre-specified secondary endpoints included transfusion avoidance, hemolysis as measured by LDH area under the curve from baseline to 26 weeks, and QoL changes as measured from baseline to 26 weeks using the Functional Assessment of Chronic Illness Therapy-Fatigue (FACIT-Fatigue) instrument.[13] Pre-specified exploratory analyses included assessment of the EORTC QLQ-C30 instrument,[14] the change in LDH from baseline through week 26, and thrombosis. Other pre-specified measurements included pharmacokinetics, pharmacodynamics, and immunogenicity of eculizumab. Time to first transfusion during the 26-week treatment phase and the proportion of PNH type III blood cells were also assessed.

Safety Assessments

Treatment-emergent adverse events, clinical laboratory tests (e.g., serum chemical analyses and complete blood counts), electrocardiogram data, and vital signs were assessed. Adverse events were defined using the MedDRA preferred terms and tabulated as incidence rates per treatment group.

Statistical Analysis

For co-primary endpoints, analyses were performed according to the intention to treat using the data from all patients who were randomized and received study drug; stabilization of hemoglobin levels was analyzed using the Fisher's exact test and total PRBC units transfused were analyzed with the Wilcoxon's rank sum test. For comparison of treatment effect on transfusion avoidance, the Fisher's exact test was used on the incidence and the log rank test was used for time to first transfusion. For LDH area under the curve the Wilcoxon's rank sum test was used.

Quality of life measure of fatigue was assessed using the scoring guidelines for the FACIT-Fatigue instrument.[15] Assessment of quality of life measures based on the EORTC QLQ-C30 instrument was conducted in accordance with the appropriate scoring guidelines.[16] The changes of FACIT-Fatigue and EORTC QLQ-C30 scores from baseline through 26 weeks were analyzed using a mixed model, with baseline as covariate, treatment and time as fixed effects, and patient as a random effect. Changes in LDH levels and PNH type HI erythrocytes from baseline through 26 weeks were analyzed using the same mixed model. Two-sided tests were used for all analyses. The adverse events and long-term safety checklist were tabulated separately and compared between treatments using the Fisher's exact test. A p-value≤0.05 was considered to be statistically significant.

Results

Characteristics of Patients

A total of 115 PNH patients were screened. Six patients did not meet the inclusion/exclusion criteria during the screening period. Twenty-one other patients did not receive a qualifying transfusion and were not randomized into the treatment phase. One patient who did not meet the inclusion criteria was inadvertently randomized, but did not receive study medication. Thus 87 hemolytic PNH patients (35 men and 52 women) were enrolled and randomized to receive either eculizumab (N=43) or placebo (N=44), exceeding the original target of 75 randomized patients.

Patient characteristics were similar in the eculizumab- and placebo-treated cohorts: median age, 41 (range 20-85) and 35 (range 18-78) years; median duration of PNH, 4.2 (range 0.8 to 29.7) and 9.2 (range 0.4 to 38.3) years; patients with history of aplastic anemia, 4 and 11; history of myelodysplastic syndrome, 1 and 0; and history of thrombosis, 9 (16 events) and 8 (11 events). Stable usage of concomitant medications at baseline in the eculizumab- and placebo-treated groups included the following: erythropoietin, 3 patients and 0 patients; cyclosporine, 1 and 1; anticoagulants (coumarins or heparins) 21 and 11; and steroids (glucocorticoids or androgenic steroids), 12 and 12, respectively.

Of the 87 patients randomized, 85 completed the trial. Two patients who did not complete the trial had been randomized to the eculizumab arm: one patient discontinued due to the inconvenience of travel to the study site and the second patient became pregnant. Ten patients in the placebo-treatment group discontinued infusions, in all cases due to perceived lack of efficacy, but they remained in the study for monitoring purposes.

Pharmokinetics/Pharmacodynamics

In 42 of the 43 eculizumab-treated patients the levels of drug during the maintenance period (900 mg every 2 weeks±2 days) were sufficient to completely block serum hemolytic activity (mean trough value at week 26 of 101.8 µg/mL). A single patient did not sustain therapeutic trough levels of eculizumab and demonstrated a breakthrough in complement blockade during the last few days of each dosing interval. These breakthroughs were clinically manageable and quickly resolved following the next dose.

Hemolytic Efficacy Variables

The impact of terminal complement inhibition with eculizumab on chronic intravascular hemolysis in PNH patients was demonstrated in this study by an immediate (one week) and sustained decrease in mean levels of LDH (FIG. 1A). The median LDH area under the curve during the 26-week study period was reduced 85.8% in eculizumab-relative to placebo-treated patients (P<0.001). The mean LDH level decreased from 2199.7±157.7 IU/L at baseline to 327.3±67.6 IU/L by 26 weeks in eculizumab-treated patients while levels in placebo-treated patients remained consistently elevated with values of 2259.0±158.5 IU/L at baseline and 2418.9*140.3 IU/L at 26 weeks (P<0.001, for eculizumab versus placebo). A second biochemical measure of hemolysis, serum aspartate aminotransferase (AST), also showed a statistically significant improvement following eculizumab- versus placebo-treatment (data not shown). Haptoglobin levels were statistically significantly increased in eculizumab—as compared to placebo-treated patients but mean levels of haptoglobin were still below normal levels in eculizumab-treated patients (data not shown).

Figure 1B:
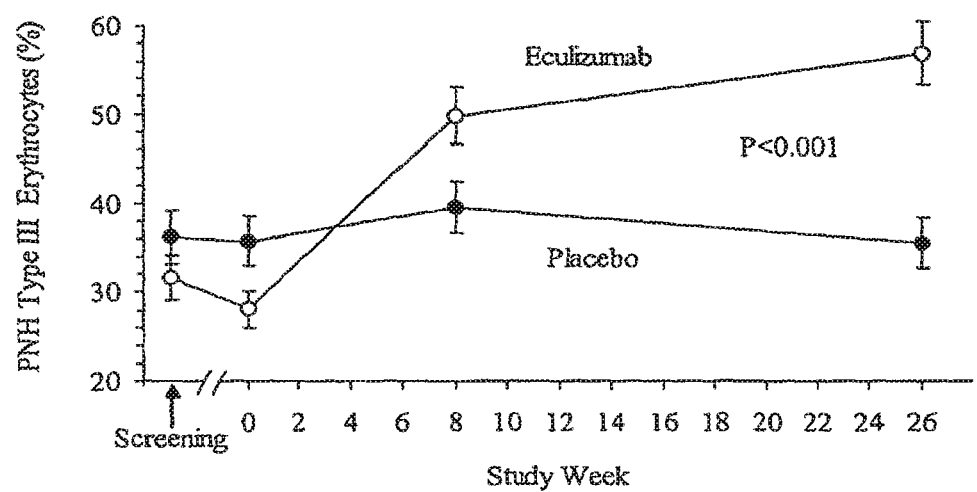

FIG. 1A shows the degree of intravascular hemolysis in PNH patients, demonstrated by mean lactate dehydrogenase (LDH) levels (±standard error) from baseline (study week 0) to week 26 for both eculizumab- and placebo-treated patient populations. Screening occurred up to 3 months prior to study week 0. The upper limit of the normal range (103-223 IU/L) for LDH is indicated by a dashed line. LDH was reduced to a mean level just above the upper limit of normal at week 26 for eculizumab-treated patients; 15 of 41 patients who completed the study demonstrated LDH levels within the normal range. All placebo-treated patients remained at least 5 times above the upper limit of normal at week 26. The P value is based on a mixed model analysis from baseline through week 26. FIG. 1B shows the mean proportion (±standard error) of PNH type III erythrocytes assessed for placebo- and eculizumab-treated patients. The screening visit occurred up to 3 months prior to study week 0. The P value is based on a mixed model analysis from baseline through week 26.

A corollary to the reduction in intravascular hemolysis during eculizumab treatment was an observed increase in the PNH type III erythrocyte population (FIG. 1B). The mean proportions of type III erythrocytes increased from 28.1±12.0% at baseline to 56.9±3.6% by week 26 for eculizumab-treated patients while proportions in the placebo group remained constant with mean values of 35.7±2.8% before treatment to 35.5±2.8% at 26 weeks (P<0.001, for eculizumab versus placebo). By contrast, the proportions of PNH type III granulocytes and monocytes did not change significantly between the treatment groups during the treatment period and were greater than 90% at week 26.

Clinical Efficacy

Co-primary Endpoints

The co-primary efficacy endpoints in the TRIUMPH trial were stabilization of hemoglobin levels and reduction in PRBC units transfused. At the end of the treatment period, 48.8% of eculizumab-treated patients had maintained levels of hemoglobin above the pre-specified set-point (median set-point value of 7.7 g/dL for both treatment groups) in the absence of transfusions, whereas stabilization of hemoglobin did not occur in any of the patients in the placebo group (P<0.001; Table 1). By week 26, the median of PRBC units transfused per patient was 0 in the eculizumab group and 10.0 in the placebo cohort (P<0.001), while the mean of PRBC units transfused was 3.0 and 11.0 in the eculizumab and placebo cohorts, respectively. In the 6-month period prior to the study, the median of PRBC units transfused per patient was 9.0 in the eculizumab cohort and 8.5 in placebo patients while the mean of PRBC units transfused was 9.6±0.6 and 9.7±0.7, respectively. Mean hemoglobin levels were similar between the treatment groups at baseline (10.0±1.8 g/dL in eculizumab-treated patients and 9.7±1.8 g/dL in placebo-treated patients) and did not substantially change by week 26 (10.1±2.5 g/dL and 8.9±2.2 g/dL in eculizumab and placebo cohorts, respectively).

Figure 2:
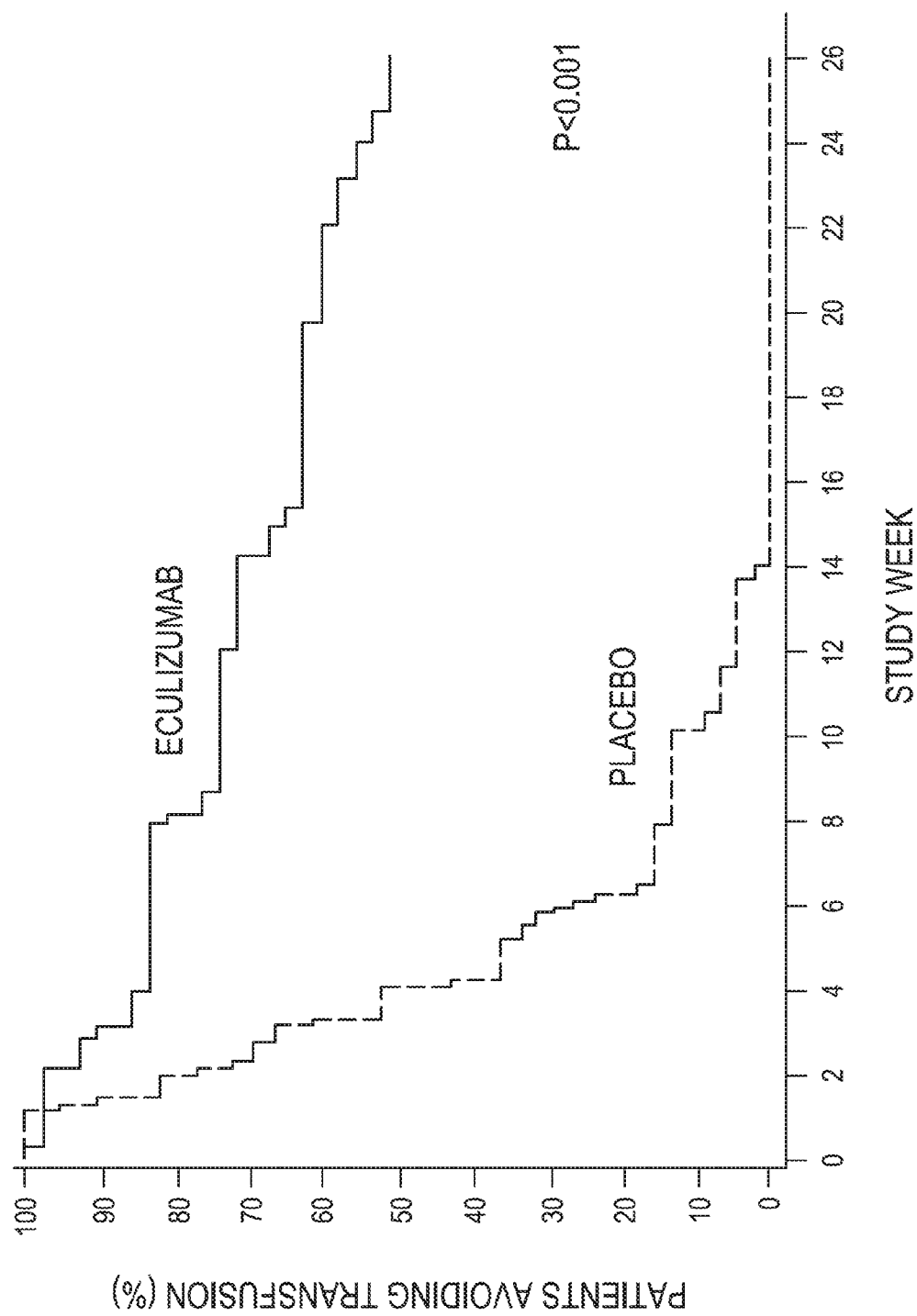
FIG. 2 shows the effect of eculizumab treatment on transfusion requirements in PNH patients. This is a Kaplan-Meier plot of time to first transfusion for eculizumab- and placebo-treated patients from baseline through week 26. The P value is from the log rank analysis.

The median time to first transfusion was not reached during the study period in eculizumab-treated patients (it was greater than 26 weeks) while the placebo group reached the median time to first transfusion in only 4 weeks (P<0.001; FIG. 2). Transfusion avoidance was achieved in 51.2% and 0% of the eculizumab and placebo cohorts, respectively (P<0.001). By the end of the 26-week treatment period, the total PRBC units transfused were 131 in eculizumab-treated patients versus 482 in the placebo group (Table 1). By contrast, in the 6-month period prior to the study, total PRBC units transfused in the eculizumab- and placebo-cohorts were 413 and 417, respectively.

TABLE 1

Stabilization of Hemoglobin Levels and Reduction in Transfusion Requirements during Eculizumab Treatment

| | PRE-TREATMENT HISTORY* | | TREATMENT PERIOD | | |
|---|---|---|---|---|---|
| | Placebo | Eculizumab | Placebo | Eculizumab | P Value |
| †Stabilization of Hemoglobin Levels in the absence of transfusions (percent of patients) | NA | NA | 0 | 48.8 | <0.001‡ |
| †Units Transfused per Patient | | | | | |
| Median | 8.5 | 9.0 | 10 | 0 | <0.001§ |
| Mean ± SE | 9.7 ± 0.7 | 9.6 ± 0.6 | 11.0 ± 0.83 | 3.0 ± 0.67 | |
| Total Units Transfused per Group | 417 | 413 | 482 | 131 | |

Figure 3:
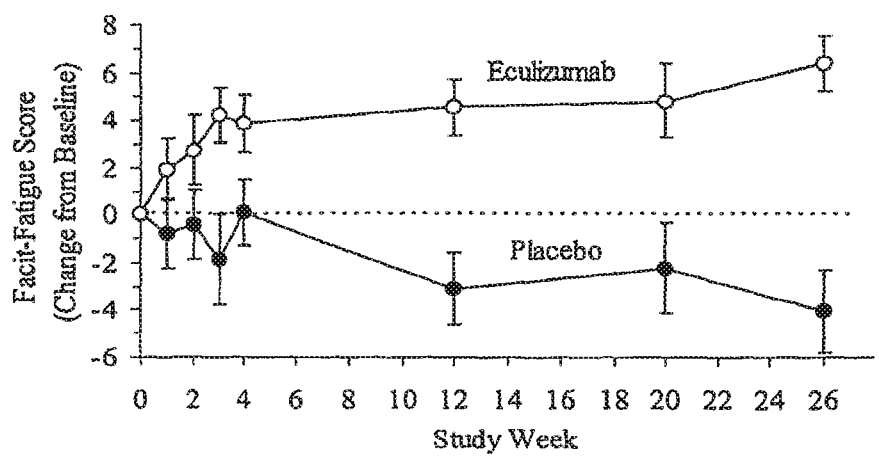
FIG. 3 shows the effect of eculizumab on fatigue assessed by the FACIT-Fatigue Instrument Quality of Life scores were assessed using the Functional Assessment of Chronic Illness Therapy-Fatigue (FACIT-Fatigue) instrument. Values for change from baseline to 26 weeks represent least-square means. A positive change indicates an improvement and a negative change indicates deterioration in the FACIT-Fatigue measures of quality of life.

*Twelve month historical transfusion data normalized to 6 months
†Co-primary endpoints
‡Base on 2-sided Fisher's exact test
§Based on Wilcoxon's rank sum test
NA, not applicable Improvements in Quality of Life Measures Assessments of quality of life in PNH patients during eculizumab treatment were performed using two different instruments, FACIT-Fatigue and the EORTC QLQ-C30. Eculizumab-treated patients showed a mean increase (improvement) in the FACIT-Fatigue score of 6.4±1.2 points from baseline to 26-weeks while the mean score in placebo patients decreased by 4.0±1.7 points, a total difference between the treatment groups of 10.4 points (FIG. 3). Mixed model analysis of covariance demonstrated a statistically significant difference between treatment groups (P<0.001).

For the EORTC instrument, improvements were observed with eculizumab-treatment in each subscale. Statistically significant improvements with eculizumab-compared with placebo-treated groups were observed in the following quality of life subscales (Table 2): global health status (P<0.001), physical functioning (P<0.001), emotional functioning (P=0.008), cognitive functioning (P=0.002), role functioning (P<0.001), social functioning (P=0.003), fatigue (P<0.001), pain (P=0.002), dyspnea (P<0.001), appetite loss (P<0.001), and insomnia (P=0.014). The improvements with eculizumab treatment in the other scales, including nausea and vomiting, diarrhea, constipation, and financial difficulties, did not reach statistical significance.

TABLE 2

Effect of Eculizumab Treatment on Quality of Life Assessed by the EORTC QLQ-C30 Instrument

| | Mean Change from Baseline to Week 26* | | Absolute Difference | P Value† |
|---|---|---|---|---|
| | Placebo | Eculizumab | | |
| Global Health Status | −8.5 | 10.9 | 19.4 | <0.001 |
| Functional | | | | |
| Role | −6.9 | 17.9 | 24.8 | <0.001 |
| Social | 2.0 | 16.7 | 14.6 | =0.003 |
| Cognitive | −6.1 | 7.9 | 14.0 | =0.002 |
| Physical | −3.5 | 9.4 | 13.0 | <0.001 |
| Emotional | −3.7 | 7.5 | 11.2 | =0.008 |
| Symptoms/Single Items | | | | |
| Fatigue | 10.0 | −16.9 | 27.0 | <0.001 |
| Pain | 5.3 | −12.3 | 17.6 | =0.002 |
| Dyspnea | 8.9 | −7.9 | 16.9 | <0.001 |
| Appetite Loss | 3.3 | −10.3 | 13.6 | <0.001 |
| Insomnia | 4.9 | −7.9 | 12.8 | =0.014 |
| Financial Difficulties | 0.0 | −10.3 | 10.3 | =0.186 |
| Constipation | 0.0 | −6.3 | 6.3 | =0.199 |
| Nausea/vomiting | 2.8 | −0.4 | 3.2 | =0.056 |
| Diarrhea | 5.7 | 4.8 | 0.9 | =0.147 |

*A positive change indicates an improvement in global health status and functional scales and a negative change indicates an improvement in symptom and single item scales.
†Based on a mixed analysis-of-covariance model with visit as a fixed effect, patient as a random effect and baseline as a covariate.

Relationship Between FACIT-Fatigue Quality of Life and Intravascular Hemolysis

In order to determine if there was a treatment independent relationship between the FACIT-Fatigue quality of life instrument and intravascular hemolysis, an analysis was performed whereby the mean LDH level (through the 26 week study period) for each TRIUMPH patient was analyzed as a function of the patient's respective mean change in FACIT-Fatigue score from baseline (through the 26 week study period) (see Table 3). For this analysis, mean levels of LDH were divided into 4 groups that included: normal levels, 1-2 times the upper limit of normal (ULN), 2-10 times the upper limit of normal, and greater than 10 times the upper limit of normal. The analysis demonstrated that patients who maintained normal LDH levels throughout the study experienced significant improvements in fatigue when compared to patients who had incrementally higher levels of LDH throughout the study (p=0.0048). These data establish a clear link between increasing intravascular hemolysis as measured by LDH levels and decreased quality of life as measured by the FACIT-Fatigue quality of life instrument.

TABLE 3

Relationship between FACIT-Fatigue and Intravascular Hemolysis

| Treatment Group | LDH Category | Change of FACIT from Baseline | | P Value |
|---|---|---|---|---|
| | | <4 | >=4 | |
| Combined | Normal | 4 (30.77%) | 9 (69.23%) | .0048 |
| | 1-2 × ULN | 16 (61.54%) | 10 (38.46%) | |
| | 2-10 × ULN | 18 (72.00%) | 7 (28.00%) | |
| | >10 × ULN | 16 (80.00%) | 4 (20.00%) | |

Safety

There were no deaths in the study. Serious adverse events (SAEs) were reported for 13 patients, of which 4 occurred in the eculizumab-treated cohort and 9 were in the placebo-treated cohort (see Table 4). All patients recovered without sequelae.

The most common AEs reported for eculizumab-treated patients were headache, nasopharyngitis, back pain, and upper respiratory tract infection. Headache and back pain occurred more commonly in the eculizumab-treatment group compared with the placebo group. However, the increase in headaches was limited to the first 2 weeks of therapy and was mild to moderate. There were no statistically significant differences in incidents rates between treatment groups for any AEs reported.

One episode of thrombosis (Budd-Chiari) occurred in a placebo-treated patient. There were no thromboses in eculizumab-treated patients.

Only one patient showed a detectable level of anti-eculizumab antibodies in the eculizumab-treated cohort; this response was weak (did not titrate), occurred at only one time point and did not result in a disruption of complement blockade.

TABLE 4

Adverse Event Reporting

| | Placebo Patients n (percent) | Eculizumab Patients n (percent) |
|---|---|---|
| SERIOUS ADVERSE EVENTS* | | |
| Total | 9 (20.5) | 4 (9.3) |
| Eculizumab treatment emergent | | |
| Exacerbation of PNH | 3 (6.8) | 1 (2.3) |
| Renal colic | 0 | 1 (2.3) |
| Lumbar sacral disc prolapse | 0 | 1 (2.3) |
| Alpha streptococcal bacteremia | 0 | 1 (2.3) |
| Central line infection and UTI | 1 (2.3) | 0 (0) |
| Upper respiratory tract infection | 1 (2.3) | 0 (0) |
| Probable viral infection | 1 (2.3) | 0 (0) |
| Neutropenia | 1 (2.3) | 0 (0) |
| Cellulitis/folliculitis/neutropenia | 1 (2.3) | 0 (0) |
| Anemia and pyrexia | 1 (2.3) | 0 (0) |
| MOST FREQUENT ADVERSE EVENTS*† | | |
| Headache§ | 12 (27.3) | 19‡ (44.2) |
| Nasopharyngitis | 8 (18.2) | 10 (23.3) |
| Upper respiratory tract infection | 10 (22.7) | 6 (14) |
| Back pain | 4 (9.1) | 8 (18.6) |
| Nausea | 5 (11.4) | 7 (16.3) |
| Cough | 4 (9.1) | 5 (11.6) |
| Diarrhea | 5 (11.4) | 4 (9.3) |
| Arthralgia | 5 (11.4) | 3 (7.0) |
| Abdominal pain | 5 (11.4) | 2 (4.7) |
| Dizziness | 5 (11.4) | 2 (4.7) |
| Vomiting | 5 (11.4) | 2 (4.7) |
| Fatigue | 1 (2.3) | 5 (11.6) |
| Viral infection | 5 (11.4) | 1 (2.3) |

*By preferred terms
†Occurring in 10% or more of patients
‡Sixteen of 19 patients experienced headache within 48 hours of infusion
§Following the first 2 weeks of dosing, 20.9% of eculizumab- and 22.7% of placebo-treated patients experienced headache Discussion Chronic intravascular hemolysis with periods of acute exacerbation are the classical manifestations of PNH, frequently resulting in anemia, the need for transfusions to sustain hemoglobin levels, and deterioration in quality of life. In the phase III pivotal TRIUMPH study, we examined the effect of terminal complement inhibition with eculizumab on hemoglobin levels and transfusion requirements in patients with PNH. Forty-nine percent of patients treated with eculizumab over the 6-month period demonstrated stabilization of hemoglobin in the absence of transfusions compared to no patients in the placebo arm of the trial. Over 50% of eculizumab-treated patients were transfusion independent during the entire study compared to none in the placebo arm, and the overall mean transfusion rate was reduced by 73%. Moreover, even in patients who did not achieve transfusion independence, eculizumab treatment was associated with a 44% reduction in the rate of transfusion (data now shown).

Lactate dehydrogenase, a biochemical marker of hemolysis in PNH,[9] was immediately and consistently decreased in all eculizumab-treated patients, while patients in the placebo cohort continued to hemolyze with levels of LDH exceeding 5 times the upper limit of the normal range in all patients at the study end. Levels of LDH were reduced into the normal range in approximately one-third of eculizumab-treated patients, while the remainder stabilized at a level just above the upper limit of normal suggesting residual low level hemolysis in some patients. Levels of haptoglobin, a more sensitive marker of the presence of cell free hemoglobin in the circulation, were undetectable in most patients. Low level hemolysis in a subset of eculizumab-treated patients is possibly due to an inherent decrease in survival of these cells or C3b-mediated, extravascular clearance of PNH erythrocytes through the reticuloendothelial system.[17]

Before eculizumab treatment, hemoglobin levels in study patients were artificially maintained by frequent transfusion. Therefore, stabilization of hemoglobin levels with a concomitant cessation of or reduction in transfusions represents a net increase in endogenous hemoglobin levels. Our data suggest that resolution of hemolysis with eculizumab results in a new steady state hemoglobin level determined by a balance between the extent of the underlying bone marrow dysfunction, the number of PNH erythrocytes that are preserved by eculizumab therapy and the new level (if any) of transfusion requirement.

Patients with PNH generally experience markedly impaired quality of life characterized by fatigue, anemia, thrombosis, and pulmonary hypertension as well as smooth muscle dystonia including abdominal pain, dysphagia, and erectile dysfunction.[9,10,18] These symptoms have been attributed to both excessive intravascular hemolysis and downstream scavenging of nitric oxide by cell free hemoglobin in plasma. The reduction of intravascular hemolysis in eculizumab-treated patients in the current study was associated with significant improvements in the fatigue component of quality of life relative to placebo-treated patients as assessed via the FACIT-Fatigue instrument. Further, eculizumab therapy was associated with a median increase of 6.4 points over baseline values established before treatment. It has previously been demonstrated that an increase of 3 or more points from baseline represents a clinically important difference in this quality of life instrument.[19] Patients who received eculizumab also experienced a significant improvement in most domains of the EORTC QLQ-30 relative to the placebo-treated cohort including global health status, physical functioning, emotional functioning cognitive functioning, role functioning, social functioning, fatigue, pain, dyspnea, appetite loss, and insomnia. Improvement in the fatigue component of the EORTC QLQ-30 provides support for the improvement demonstrated in the FACIT-Fatigue instrument during eculizumab therapy. Importantly, these improvements in quality of life in the eculizumab-treated patients occurred despite similar levels of erythrocyte hemoglobin in the two treatment groups, further supporting the contribution of hemolysis per se, as opposed to anemia, in mediating the poor quality of life in PNH patients. Clinical assessment of additional life quality-related symptoms of PNH, including abdominal pain, dysphagia, and erectile dysfunction, have also been reported to improve during eculizumab therapy.[20]

Eculizumab was safe and well-tolerated. There were no deaths in the study and only a single thrombotic event which occurred in a placebo patient in a site (the hepatic veins) which is typical of the thrombosis in PNH. The relative brief duration of this study was not sufficient to address the relevant issue of a possible protection from thrombosis by terminal complement inhibition with eculizumab.

Adverse events were generally mild with headache occurring at increased frequency in the eculizumab-treated patients; however, this increased frequency did not persist following the first two doses of therapy. There were 4 SAEs in the eculizumab treatment group and 9 SAEs in the placebo group. There was no evidence of increased infection risk in eculizumab-treated patients during the study period. One eculizumab-treated patient showed 8 low level of anti-eculizumab antibodies at one time point during the study which did not persist and did not result in a disruption of complement blockade. There were no AEs associated with eculizumab withdrawal in the 2 eculizumab-treated patients who did not complete the trial. Additional safety assessments, as well as efficacy measures, are being examined in an ongoing multi-center, open-label Phase III safety trial of eculizumab (SHEPHERD) in approximately 95 patients with PNH.

Results from the current randomized, double-blind, placebo-controlled, global study show that terminal complement inhibition with eculizumab appears to be a safe and effective therapy for patients with the rare disorder PNH. Treatment with eculizumab reduced intravascular hemolysis, and stabilized hemoglobin levels despite a reduction of transfusions, to the point where most PNH patients were rendered transfusion independent Substantial and clinically meaningful improvements in fatigue and other key quality of life parameters were also demonstrated. All of the 85 patients who completed the study elected to receive eculizumab in an open-label extension study and all currently remain on drug. The results of the TRIUMPH study indicate that terminal complement inhibition with eculizumab safely and effectively addresses an important consequence of the underlying genetic defect in PNH hematopoietic stem cells by providing a therapeutic replacement for the terminal complement inhibitor deficiency.

The present invention provides among other things treatment with an inhibitor of complement. Many variations of the invention will become apparent to those skilled in the art upon review of this specification. The full scope of the invention should be determined by reference to the claims, along with their full scope of equivalents, and the specification, along with such variations.

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

1. Takeda J, Miyata T, Kawagoe K et al. Deficiency of the GPI anchor caused by a somatic mutation of the PIG-A gene in paroxysmal nocturnal hemoglobinuria. Cell 1993; 73:703-11.
2. Bessler M, Mason P J, Hillmen P et al. Paroxysmal nocturnal haemoglobinuria (PNH) is caused by somatic mutations in the PIG-A gene. EMBO J 1994;13:110-7.
3. Yamashina M, Ueda E, Kinoshita T et al. Inherited complete deficiency of 20-kilodalton homologous restriction factor (CD59) as a cause of paroxysmal nocturnal hemoglobinuria. N Engl J Med 1990;323:1184-9.
4. Motoyama N, Okada N, Yamashina M, Okada H. Paroxysmal nocturnal hemoglobinuria due to hereditary nucleotide deletion in the HRF20 (CD59) gene. Eur J Immunol 1992; 22:2669-73.
5. Holguin M H, Fredrick L R, Bemshaw N J, Wilcox L A, Parker C J. Isolation and characterization of a membrane protein from normal human erythrocytes that inhibits reactive lysis of the erythrocytes of paroxysmal nocturnal hemoglobinuria. J Clin Invest 1989;84:7-17.
6. Rollins S A, Sims P J. The complement-inhibitory activity of CD59 resides in its capacity to block incorporation of C9 into membrane C5b-9. J Immunol 1990;144:3478-83.

7. Sims P J, Rollins S A, Wiedmer T. Regulatory control of complement on blood platelets. Modulation of platelet procoagulant responses by a membrane inhibitor of the C5b-9 complex. J Biol Chem 1989;264:19228-35.
8. Wiedmer T, Hall S E, Ortel T L, Kane W H, Rosse W F, Sims P J. Complement-induced vesiculation and exposure of membrane prothrombinase sites in platelets of paroxysmal nocturnal hemoglobinuria. Blood 1993;82:1192-6.
9. Rother R P, Bell L, Hillmen P, Gladwin M T. The clinical sequelae of intravascular hemolysis and extravascular plasma hemoglobin: a novel mechanism of human disease. JAMA 2005;293:1653-62.
10. Rosse W F. Paroxysmal nocturnal hemoglobinuria. Hoffman. New York: Churchill Livingstone, 2000: 331-342.
11. Thomas T C, Rollins S A, Rother R P et al. Inhibition of complement activity by humanized antibody that binds C5 and single-chain Fv. Mol Immunol 1996;33:1389-401.
12. Hillmen P, Hall C, Marsh J C et al. Effect of eculizumab on hemolysis and transfusion requirements in patients with paroxysmal nocturnal hemoglobinuria. N Engl J Med 2004;350:552-9.
13. Yellen S B, Celia D F, Webster K, Blendowski C, Kaplan E. Measuring fatigue and other anemia-related symptoms with the Functional Assessment of Cancer Therapy (FACT) measurement system. J Pain Symptom Manage 1997;13:63-74.
14. Aaronson N K, Ahmedzai S, Bergman B et al. The European Organization for Research and Treatment of Cancer QLQ-C30: a quality-of-life instrument for use in international clinical trials in oncology. J Natl Cancer Inst 1993;85:365-76.
15. Cella D. Manual of the Functional Assessment of Chronic Illness Therapy (FACIT)
Measurement System. Version 4. Center on Outcomes Research and Education (CORE) Evanston Northwestern Healthcare and Northwestern University, 1997.
16. Fayers P M, Aaronson N K, Bjordal K et al. The EORTC QLQ-C30 Scoring Manual (3rd Edition). Brussels: European Organisation for Research and Treatment of Cancer, 2001.
17. Jasinski M, Pantazopoulos P, Rother R P et al. A novel mechanism of complement-independent clearance of red cells deficient in glycosyl phosphatidylinositol-linked proteins. Blood 2004;103:2827-34.
18. Hill A, Wang X, Sapsford R J et al. Nitric oxide Consumption and Pulmonary Hypertension in Patients with Paroxysmal Nocturnal Hemoglobinuria. Blood 106 [11]. 2005. Ref Type: Abstract
19. Cella D, Eton D T, Lai J S, Peterman A H, Merkel D E. Combining anchor and distribution-based methods to derive minimal clinically important differences on the Functional Assessment of Cancer Therapy (FACT) anemia and fatigue scales. J Pain Symptom Manage 2002; 24:547-61.
20. Hill A, Rother R P, Hillmen P. Improvement in the symptoms of smooth muscle dystonia during eculizumab therapy in paroxysmal nocturnal hemoglobinuria. Haematologica 2005;90:ECR40.
21. Parker C, Omine M, Richards S et al. Diagnosis and management of paroxysmal nocturnal hemoglobinuria. Blood 2005;106:3699-709.
22. Hill A, Wang X, Sapsford R J et al. Nitric oxide Consumption and Pulmonary Hypertension in Patients. with Paroxysmal Nocturnal Hemoglobinuria. Blood 2005;106:A1046.

SEQUENCES
Eculizumab $V_H$

SEQ ID NO: 1
QVQLVQSGAEVKKPGASVKVSCKASGYIFSNYWIQWVRQAPGQGLEWMG

EILPGSGSTEYTENFKDRVTMTRDTSTSTVYMELSSLRSEDTAVYYCAR

YFFGSSPNWYFDVWGQGTLVTVSSA

Eculizumab Heavy chain

SEQ ID NO: 2
QVQLVQSGAEVKKPGASVKVSCKASGYIFSNYWIQWVRQAPGQGLEWMG

EILPGSGSTEYTENFKDRVTMTRDTSTSTVYMELSSLRSEDTAVYYCAR

YFFGSSPNWYFDVWGQGTLVTVSSASTKGPSVFPLAPCSRSTSESTAAL

GCLVKDYFPEPVTVSWNSGALTSGVHTFPAVLQSSGLYSLSSVVTVPSS

NFGTQTYTCNVDHKPSNTKVDKTVERKCCVECPPCPAPPVAGPSVFLFP

PKPKDTLMISRTPEVTCVVVDVSQEDPEVQFNWYVDGVEVHANKTKPRE

EQFNSTYRVVSVLTVLHQDWLNGKEYKCKVSNKGLPSSIEKTISKAKGQ

PEPEQVYTLPPSQEEMTKNQVSLTCLVKGFYPSDIAVEWESNGQPENNY

KTTPPVLDSDGSFFLYSRLTVDKSRWQEGNVFSCSVMHEALHNHYTQKS

LSLSLGK

Eculizumab $V_L$

SEQ ID NO: 3
MDMRVPAQLLGLLLLSLRGARCDIQMTQSPSSLSASVGDRVTITCGASE

NIYGALNWYQQKPGKAPKLLIYGATNLADGVPSRFSGSGSGTDFTLTIS

SLQPEDFATYYCQNVLNTPLTFGQGTKVEIKRT

Eculizumab Light chain

SEQ ID NO: 4
DIQMTQSPSSLSASVGDRVTITCGASENIYGALNWYQQKPGKAPKLLIY

GATNLADGVPSRFSGSGSGTDFTLTISSLQPEDFATYYCQNVLNTPLTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Eculizumab CDRH1

SEQ ID NO: 5
NYWIQ

Eculizumab CDRH2

SEQ ID NO: 6
EILPGSGSTEYTENFKD

Eculizumab CDRH3

SEQ ID NO: 7
YFFGSSPNWYFDV

Eculizumab CDRL1

SEQ ID NO: 8
GASENIYGALN

Eculizmuab CDRL2

SEQ ID NO: 9
GATNLAD

Eculizumab CDRL3

SEQ ID NO: 10
QNVLNTPLT

What is claimed is:

1. A pharmaceutical composition for use in treating a patient afflicted with paroxysmal nocturnal hemoglobinuria (PNH), wherein the composition is a sterile, preservative free, 300 mg single-use dosage form comprising 30 ml of a 10 mg/ml antibody solution, wherein the antibody comprises a heavy chain consisting of SEQ ID NO: 2 and a light chain consisting of SEQ ID NO: 4.

2. A pharmaceutical composition comprising an anti-C5 antibody, wherein the anti-C5 antibody comprises a heavy chain consisting of SEQ ID NO: 2 and a light chain consisting of SEQ ID NO: 4.

3. The pharmaceutical composition of claim 2, wherein the pharmaceutical composition is a sterile, preservative free 300 mg single-use dosage form comprising 30 ml of a 10 mg/ml anti-C5 antibody solution.

* * * * *

UNITED STATES PATENT AND TRADEMARK OFFICE
CERTIFICATE OF CORRECTION

PATENT NO. : 9,718,880 B2
APPLICATION NO. : 15/148839
DATED : August 1, 2017
INVENTOR(S) : Leonard Bell et al.

It is certified that error appears in the above-identified patent and that said Letters Patent is hereby corrected as shown below:

On the Title Page

Item (56)

On page 2, in Column 1, under "Other Publications", Line 6, delete "Nocturanl" and insert -- Nocturnal --, therefor.

On page 2, in Column 1, under "Other Publications", Line 8, delete "identifer" and insert -- identifier --, therefor.

On page 2, in Column 1, under "Other Publications", Line 15, delete "Rather" and insert -- Rother --, therefor.

On page 2, in Column 1, under "Other Publications", Line 19, delete ""Solids" and insert -- "Soliris --, therefor.

On page 2, in Column 2, under "Other Publications", Line 17, delete "EMAIHMPC" and insert -- EMA/HMPC --, therefor.

On page 2, in Column 2, under "Other Publications", Line 38, delete "Dsborne," and insert -- Osborne, --, therefor.

On page 2, in Column 2, under "Other Publications", Line 40, delete "Dsbourn," and insert -- Osbourn, --, therefor.

On page 3, in Column 1, under "Other Publications", Line 1, delete "2007," and insert -- 2006, --, therefor.

Signed and Sealed this
Twenty-fourth Day of October, 2017

Joseph Matal
*Performing the Functions and Duties of the
Under Secretary of Commerce for Intellectual Property and
Director of the United States Patent and Trademark Office*

On page 3, in Column 1, under "Other Publications", Lines 18-19, delete "mi mOYUG/is 1 14/ai 17208612" and insert -- mimOYUG/is114/ai17208612 --, therefor.

On page 3, in Column 1, under "Other Publications", Line 23, delete "sub press.cfm" and insert -- subpress.cfm --, therefor.

On page 3, in Column 1, under "Other Publications", Line 35, delete "Insrum." and insert -- Instrum. --, therefor.

On page 3, in Column 1, under "Other Publications", Line 42, delete "Neisseia" and insert -- Neisseria --, therefor.

On page 3, in Column 1, under "Other Publications", Line 53, delete "sub press." and insert -- subpress. --, therefor.

On page 3, in Column 1, under "Other Publications", Line 56, delete "Hemoglobinuira" and insert -- Hemoglobinuria --, therefor.

On page 3, in Column 1, under "Other Publications", Line 59, delete "view newsitem.aspx" and insert -- viewnewsitem.aspx --, therefor.

On page 3, in Column 1, under "Other Publications", Line 60, delete "Phamaceuticals:" and insert -- Pharmaceuticals: --, therefor.

On page 3, in Column 1, under "Other Publications", Line 64, delete "Pharmaceuitcals" and insert -- Pharmaceuticals --, therefor.

On page 3, in Column 2, under "Other Publications", Line 2, delete "Domponent,"" and insert -- component," --, therefor.

On page 3, in Column 2, under "Other Publications", Line 17, delete "hourse;" and insert -- horse; --, therefor.

On page 3, in Column 2, under "Other Publications", Line 40, delete "membranetargeted" and insert -- membrane targeted --, therefor.

On page 3, in Column 2, under "Other Publications", Line 41, delete "107(5)2131-2137" and insert -- 107(5):2131-2137 --, therefor.

On page 3, in Column 2, under "Other Publications", Line 53, delete "hemglobinuria,"" and insert -- hemoglobinuria," --, therefor.

On page 3, in Column 2, under "Other Publications", Line 53, delete "Hermal." and insert -- Hematol. --, therefor.

On page 3, in Column 2, under "Other Publications", Line 64, delete "17:125-132" and insert -- 77:125-132 --, therefor.

On page 3, in Column 2, under "Other Publications", Line 70, delete "iocturnal" and insert -- nocturnal --, therefor.

On page 4, in Column 2, under "Other Publications", Line 6, delete "modem" and insert -- modern --, therefor.

On page 4, in Column 2, under "Other Publications", Line 15, delete "Medelian" and insert -- Mendelian --, therefor.

In the Specification

In Column 1, Line 23, delete "Seq _Listing.txt" and insert -- Seq_Listing.txt --, therefor.

In Column 1, Lines 45-46, delete "heomoglobinuria" and insert -- hemoglobinuria --, therefor.

In Column 1, Line 66, delete "II" and insert -- III --, therefor.

In Column 4, Line 2, delete "antibodies" and insert -- antibodies, --, therefor.

In Column 4, Line 43, delete "NO:5," and insert -- NO: 5, --, therefor.

In Column 4, Line 43, delete "NO:6," and insert -- NO: 6, --, therefor.

In Column 4, Line 44, delete "NO:7," and insert -- NO: 7, --, therefor.

In Column 4, Line 47, delete "NO:8," and insert -- NO: 8, --, therefor.

In Column 4, Line 47, delete "NO:9," and insert -- NO: 9, --, therefor.

In Column 4, Line 47, delete "NO:10." and insert -- NO: 10. --, therefor.

In Column 5, Line 45, delete "Instrument" and insert -- Instrument. --, therefor.

In Column 6, Line 33, delete "READMB.htm-1)" and insert -- README.html) --, therefor.

In Column 7, Line 49, delete "Neisseia" and insert -- Neisseria --, therefor.

In Column 7, Line 57, delete "scrum" and insert -- serum --, therefor.

In Column 7, Line 57, delete "T," and insert -- I, --, therefor.

In Column 8, Line 48, delete "at" and insert -- et --, therefor.

CERTIFICATE OF CORRECTION (continued)
U.S. Pat. No. 9,718,880 B2

In Column 8, Line 53, delete "Measurer" and insert -- Measures --, therefor.

In Column 9, Line 51, delete "if" and insert -- life --, therefor.

In Column 10, Line 28, delete "(RNAI)" and insert -- (RNAi) --, therefor.

In Column 10, Line 54, delete "Antibodies" and insert -- antibodies --, therefor.

In Column 11, Line 32, delete "2d" and insert -- $2^{nd}$ --, therefor.

In Column 12, Line 8, delete "anaphylatoxic" and insert -- anaphylatoxin --, therefor.

In Column 12, Line 22, delete "at" and insert -- et --, therefor.

In Column 12, Line 30, delete "at" and insert -- et --, therefor.

In Column 12, Line 41, delete "immunopharmaccticals" and insert -- immunopharmaceuticals --, therefor.

In Column 13, Line 15, delete "F(ab')2" and insert -- F(ab')$_2$ --, therefor.

In Column 13, Line 45, delete "at" and insert -- et --, therefor.

In Column 13, Line 56, delete "at" and insert -- et --, therefor.

In Column 14, Line 15, delete "(see." and insert -- (see, --, therefor.

In Column 14, Line 29, delete "antibodies"" and insert -- antibodies --, therefor.

In Column 15, Line 1, delete "prepared," and insert -- prepared --, therefor.

In Column 15, Line 5, after "6,331,415;" insert -- U.S. Pat. No. --.

In Column 15, Line 10, delete "at" and insert -- et --, therefor.

In Column 15, Line 17, delete "fill-length" and insert -- full-length --, therefor.

In Column 15, Line 38, delete "at" and insert -- et --, therefor.

In Column 15, Line 39, delete "at" and insert -- et --, therefor.

In Column 15, Line 40, delete "at" and insert -- et --, therefor.

In Column 15, Line 42, delete "Method" and insert -- Methods --, therefor.

In Column 16, Line 6, delete "pet" and insert -- per --, therefor.

CERTIFICATE OF CORRECTION (continued)
U.S. Pat. No. 9,718,880 B2

In Column 18, Line 41, delete "aid" and insert -- and --, therefor.

In Column 18, Line 59, after "(mg/mL)]" insert -- . --.

In Column 19, Line 31, delete "farther" and insert -- further --, therefor.

In Column 19, Line 35, delete "needle-lees" and insert -- needle-less --, therefor.

In Column 20, Line 2, delete "meningoooccal" and insert -- meningococcal --, therefor.

In Column 20, Line 8, delete "prior-12-month" and insert -- prior 12-month --, therefor.

In Column 20, Line 14, delete "PBRC" and insert -- PRBC --, therefor.

In Column 20, Line 25, delete "level≥11.5" and insert -- level≥1.5 --, therefor.

In Column 21, Line 24, delete "HI" and insert -- III --, therefor.

In Column 21, Line 63, delete "Pharmokinetics" and insert -- Pharmacokinetics --, therefor.

In Column 22, Line 18, delete "2418.9*140.3" and insert -- 2418.9±140.3 --, therefor.

In Column 22, Line 50, delete "28.1±12.0%" and insert -- 28.1±2.0% --, therefor.

In Column 27, Lines 41-42, delete "functioning" and insert -- functioning, --, therefor.

In Column 28, Line 3, delete "8" and insert -- a --, therefor.

In Column 28, Line 21, after "independent" insert -- . --.

In Column 28, Line 60, delete "Bemshaw" and insert -- Bernshaw --, therefor.

In Column 29, Line 24, delete "Celia" and insert -- Cella --, therefor.

In Column 29, Line 52, after "Abstract" insert -- . --.

In Column 30, Line 2, delete "Patients." and insert -- Patients --, therefor.

In Column 30, Line 25, delete
"PKPKDTLMISRTPEVTCVVVDVSQEDPEVQFNWYVDGVEVHANKTKPRE" and insert
-- PKPKDTLMISRTPEVTCVVVDVSQEDPEVQFNWYVDGVEVHNAKTKPRE --, therefor.

In Column 30, Line 27, delete
"PEPEQVYTLPPSQEEMTKNQVSLTCLVKGFYPSDIAVEWESNGQPENNY and insert
-- PREPQVYTLPPSQEEMTKNQVSLTCLVKGFYPSDIAVEWESNGQPENNY --, therefor.

CERTIFICATE OF CORRECTION (continued)
U.S. Pat. No. 9,718,880 B2

In Column 30, Line 34, delete
"MDMRVPAQLLGLLLLSLRGARCDIQMTQSPSSLSASVGDRVTITCGASE" and insert
-- MDMRVPAQLLGLLLLWLRGARCDIQMTQSPSSLSASVGDRVTITCGASE --, therefor.

In Column 30, Line 61, delete "Eculizmuab" and insert -- Eculizumab --, therefor.